(12) United States Patent
Hayashi et al.

(10) Patent No.: US 12,075,775 B2
(45) Date of Patent: Sep. 3, 2024

(54) SUSTAINED-RELEASE COMPOSITE PARTICLES, METHOD FOR PRODUCING SUSTAINED-RELEASE COMPOSITE PARTICLES, DRY POWDER, AND WALLPAPER

(71) Applicant: TOPPAN PRINTING CO., LTD., Tokyo (JP)

(72) Inventors: Yumi Hayashi, Tokyo (JP); Atsuko Aoki, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 918 days.

(21) Appl. No.: 17/080,149

(22) Filed: Oct. 26, 2020

(65) Prior Publication Data
US 2021/0051950 A1   Feb. 25, 2021

Related U.S. Application Data

(63) Continuation of application No. PCT/JP2019/018046, filed on Apr. 26, 2019.

(30) Foreign Application Priority Data

Apr. 27, 2018   (JP) .................................. 2018-087498
Apr. 27, 2018   (JP) .................................. 2018-087499

(51) Int. Cl.
*A01N 25/26*   (2006.01)
*A01N 43/80*   (2006.01)
(Continued)

(52) U.S. Cl.
CPC ............. *A01N 25/26* (2013.01); *A01N 43/80* (2013.01); *A01N 57/14* (2013.01); *C05C 9/02* (2013.01); *C08F 2/44* (2013.01); *C08L 1/04* (2013.01)

(58) Field of Classification Search
CPC ........ A01N 25/26; A01N 43/80; A01N 57/14; C05C 9/02; C08F 2/44; C08L 1/04
See application file for complete search history.

(56) References Cited

U.S. PATENT DOCUMENTS 4,008,351 A * 2/1977 Inoue .................... C09J 7/22
424/114
5,489,469 A   2/1996 Kobayashi et al.
(Continued)

FOREIGN PATENT DOCUMENTS

| CN | 103665398 A | 3/2014 |
|---|---|---|
| CN | 104610703 A | 5/2015 |

(Continued)

OTHER PUBLICATIONS

Office Action issued in connection with Japanese Appl. No. 2020-515619 dated Jul. 11, 2023.
(Continued)

*Primary Examiner* — Blessing M Fubara
(74) *Attorney, Agent, or Firm* — Foley & Lardner LLP

(57) ABSTRACT

Sustained-release composite particles having improved dispersion stability and improved sustained-release properties, and exhibiting longer-term effects, a method for producing the sustained-release composite particles, a dry powder comprising the sustained-release composite particles, and wallpaper comprising the sustained-release composite particles. The sustained-release composite particles comprise core particles containing at least one type of polymer and at least one type of functional component, and micronized cellulose coating at least a part of the surface of the core particles, the core particles and the micronized cellulose being inseparable from each other.

18 Claims, 5 Drawing Sheets

(51) Int. Cl.
*A01N 57/14* (2006.01)
*C05C 9/02* (2006.01)
*C08F 2/44* (2006.01)
*C08L 1/04* (2006.01)

(56) References Cited

U.S. PATENT DOCUMENTS

| | | | |
|---|---|---|---|
| 6,117,474 | A | 9/2000 | Kamada et al. |
| 6,737,082 | B1 * | 5/2004 | Picornell Darder . A61K 31/496 424/490 |
| 2007/0098843 | A1 | 5/2007 | Tomohira |
| 2012/0283363 | A1 | 11/2012 | Kumamoto et al. |
| 2014/0037816 | A1 | 2/2014 | Bakeev et al. |
| 2014/0206798 | A1 | 7/2014 | Oomori et al. |
| 2015/0010663 | A1 * | 1/2015 | Hahn ..................... A61K 33/00 424/722 |
| 2015/0132379 | A1 * | 5/2015 | Kawano ............... A61K 9/2086 424/467 |
| 2016/0144330 | A1 | 5/2016 | Wesner et al. |
| 2016/0213782 | A1 * | 7/2016 | Remon ................. A61K 9/2031 |
| 2016/0235776 | A1 * | 8/2016 | Kulkarni ............ A61K 31/7048 |
| 2017/0058116 | A1 | 3/2017 | Ando et al. |
| 2017/0369864 | A1 * | 12/2017 | Tolia .................. A61K 47/6809 |
| 2018/0265663 | A1 | 9/2018 | Kuwagaki et al. |
| 2020/0222404 | A1 | 7/2020 | Ge et al. |
| 2020/0332040 | A1 | 10/2020 | Isogai |
| 2020/0360261 | A1 | 11/2020 | Imoto |

FOREIGN PATENT DOCUMENTS

| | | |
|---|---|---|
| CN | 105642345 A | 6/2016 |
| CN | 107129585 A | 9/2017 |
| CN | 107141387 A | 9/2017 |
| CN | 107823145 A | 3/2018 |
| CN | 107868161 A | 4/2018 |
| EP | 3 736 297 A1 | 11/2020 |
| JP | H09-208494 A | 8/1997 |
| JP | H10-7704 A | 1/1998 |
| JP | 2913093 B1 | 6/1999 |
| JP | 2000-198858 A | 7/2000 |
| JP | 2001-288273 A | 10/2001 |
| JP | 2003-146826 A | 5/2003 |
| JP | 2005-281470 A | 10/2005 |
| JP | 2006-001188 A | 1/2006 |
| JP | 2007-217557 A | 8/2007 |
| JP | 2008-001728 A | 1/2008 |
| JP | 2008-007646 A | 1/2008 |
| JP | 2010-180309 A | 8/2010 |
| JP | 2010-216021 A | 9/2010 |
| JP | 2013-014741 A | 1/2013 |
| JP | 2013-185096 A | 9/2013 |
| JP | 2014-043566 A | 3/2014 |
| JP | 2015-067573 A | 4/2015 |
| JP | 2016-155897 A | 9/2016 |
| JP | 2017-042617 A | 3/2017 |
| JP | 2017-061594 A | 3/2017 |
| JP | 2017-109946 A | 6/2017 |
| JP | 2017-114768 A | 6/2017 |
| JP | 2017-150117 A | 8/2017 |
| JP | 2017-186187 A | 10/2017 |
| JP | 2017-192897 A | 10/2017 |
| JP | 2018-140962 A | 9/2018 |
| JP | 2019-038949 A | 3/2019 |
| JP | 2019-073669 A | 5/2019 |
| KR | 100764625 B1 | 10/2007 |
| KR | 20170123099 A | 11/2017 |
| WO | WO-99/36470 A1 | 7/1999 |
| WO | WO-2007/136086 A1 | 11/2007 |
| WO | WO-2009/112836 A2 | 9/2009 |
| WO | WO-2010/095574 A1 | 8/2010 |
| WO | WO-2013/042654 A1 | 3/2013 |
| WO | WO-2014/088072 A1 | 6/2014 |
| WO | WO-2017/056908 A1 | 4/2017 |
| WO | WO-2017/219127 A1 | 12/2017 |
| WO | WO-2018/110245 A1 | 6/2018 |
| WO | WO-2018/176891 A1 | 10/2018 |
| WO | WO-2019/135384 A1 | 7/2019 |
| WO | WO-2019/151486 A1 | 8/2019 |

OTHER PUBLICATIONS

International Searching Authority, "International Search Report," issued in connection with International Patent Application No. PCT/JP2019/018046, dated Jul. 30, 2019.
International Searching Authority, "Written Opinion," issued in connection with International Patent Application No. PCT/JP2019/018046, dated Jul. 30, 2019.
Fujisawa et al., "Synthesis of Nanocellulose-stabilized Polymer Microparticles," Lecture Abstracts of the 24th Annual Meeting of the Cellulose Society of Japan, 2017, pp. 17 and 18.
Noguchi et al., "Complete nanofibrillation of cellulose prepared by phosphorylation," Cellulose, published online on Jan. 7, 2017.
Japanese Office Action issued in connection with JP Appl. Ser. No. 2019-106122 dated Mar. 22, 2023.
Database WPI; Week 201830 Thomson Scientific; London, GB; AN 2018-24451M; XP002802807.
Database WPI; Week 201830 Thomson Scientific; London, GB; AN 2018-271342; XP002802806.
Extended European Search Report dated May 7, 2021 for corresponding European Patent Application No. 19791773.5.
Cheng et al. "Effect of expanded graphite and carbon nanotubes on the thermal performance of stearic acid phase change materials," Journal of Materials Science 52: 12370-12379, 2017 (Year: 2017).
Fufisawa, et al: "Synthesis of Nanocellulose-stabilized Polymer Microparticles", 24th Annual Meeting of the Cellulose Society of Japan, Jul. 1, 2017, pp. 17-18, (with English-language machine translation, 7 pages).
Gruneberger Franziska et al: "Fibrillated 1,4-6,cellulose in heterophase polymerization of 9-12, 14 nanoscale poly(methyl methacrylate) spheres", Colloid & Polymer Science, Springer Verlag, Heidelberg, DE, vol. 294, No. 9, Jun. 11, 2016, pp. 1393-1403.
Jiao et al., "Synthesis and studies of poly(ethylene glycol dimethacrylate) microcapsule," Colloid Polym. Sci. (2016) 294:639-646. (Year: 2016).
Kalashnikova I et al: "New Pickering Emulsions stabilized by bacterial cellulose nanocrystals", Langmuir, American Chemical Society, US, vol. 27, No. 12, Jun. 21, 2011, pp. 7471-7479.
Li et al. "Cellulose nanofibers enable paraffin encapsulation and the formation of stable thermal regulation nanocomposites," Nano Energy 34:541-548, 2017 (Year: 2017).
Liu et al. "Study of Pickering emulsion stabilized by sulfonated cellulose nanowhiskers extracted from sisal fiber," Colloid and Polymer Science 293:963-974, 2015 (Year: 2015).
Liu, et al., "PMMA@SCNC composite microspheres prepared from pickering emulsion template as curcumin delivery carriers", Journal of Applied Polymer Science, (2018), (9 pages).
Noguchi et al., "Complete nanofibrillation of cellulose prepared by phosphorylation," Cellulose, published on Jan. 7, 2017.
Okada et al. "Solvent-free formation of hydroxyapatite coated biodegradable particles via nanoparticle-stabilized emulsion route," Applied Surface Science 262:39-44, 2012 (Year:2012).
Sharma et al., "Silver Nanoparticle Anchored With Novel Cross-linked Interpenetrating Polymer Networks (IPNs) and its Antibacterial Activity," Polym. Compos., 2016, p. 70. (Year: 2016).
Zhang et al. "Nanoemulsions and Nanolatexes Stabilized by Hydrophobically Functionalized Cellulose Nanocrystals," Macromolecules 50:6032-6042, 2017 (Year: 2017).
Zhang, et al., "Cellulose nanofibril-reinforced biodegradable polymer composites obtained via a Pickering emulsion approach", Cellulose 24:3313-3322, (2017).
Office Action dated Jan. 5, 2022 issued in a corresponding Chinese Patent Application No. 2019800272562.2, (11 pages).
Office Action issued in corresponding Chinese Patent Application No. 202080041771.9 dated Jan. 31, 2024 (23 pages).

\* cited by examiner

SUSTAINED-RELEASE COMPOSITE PARTICLES, METHOD FOR PRODUCING SUSTAINED-RELEASE COMPOSITE PARTICLES, DRY POWDER, AND WALLPAPER

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2019/018046, filed on Apr. 26, 2019, which is based upon and claims the benefit of priority to Japanese Patent Applications Nos. 2018-087498 and 2018-087499, both filed on Apr. 27, 2018; the disclosures of which are all incorporated herein by reference in their entireties.

TECHNICAL FIELD

The present invention relates to sustained-release composite particles encapsulating a functional component, a method for producing the sustained-release composite particles, a dry powder comprising the sustained-release composite particles, and wallpaper comprising the sustained-release composite particles.

BACKGROUND ART

Background

Conventionally, various microparticles and microcapsules have been put into practical use as functional materials in various fields. Microparticles are generally micro-size order particles formed from various polymers, and are used, for example, as fillers, spacers, abrasives, and the like.

By encapsulating drugs, pesticides, perfumes, etc., in microparticles, the encapsulated substances can be sustained-released, and their effects can be maintained for a long period of time. As a method for producing microparticles, for example, a solvent evaporation method is known in which a polymer dissolved in an organic solvent is dispersed in water using a surfactant to form an oil-in-water (O/W) emulsion encapsulating a functional component, and then the solvent is evaporated to solidify the emulsion as microparticles (PTL 1). Microparticles obtained by such a method have no self-dispersibility in water, and it is indispensable to add an auxiliary agent, such as a surfactant, during production. In addition, the functional component may be lost during the production of microparticles.

It has been attempted to impart and express further functionality by forming a microcapsule (core-shell) structure in which a microparticle is used as a core substance, and the particle surface is coated with a wall membrane. Specifically, functional components, such as magnetic substances, drugs, pesticides, perfumes, adhesives, enzymes, pigments, and dyes, are incorporated into the core substance and then converted into microcapsules, whereby the functional materials can be protected, and the release behavior can be controlled. It is also possible to further add a functional material to the wall membrane itself, which coats the core substance. PTL 2 discloses microcapsules having sustained-release properties and encapsulating an antiseptic fungicide. However, the microcapsules disclosed in PTL 2 have poor dispersibility, which causes a problem difficulty in redispersion.

As described above, since micro-size order microparticles and microcapsules have a high specific surface area, they are generally likely to aggregate, and the dispersion stability is problematic. In addition, their production methods are complicated, and it is required to efficiently encapsulate functional components. Further, they are used in the environment or in the living body depending on the application; thus, biodegradability and biocompatibility are required.

On the other hand, approaches have been actively taken to utilize cellulose fibers from wood as a novel functional material by micronizing them until at least one side of the structure thereof becomes nanometer-order length.

For example, PTL 3 discloses that micronized cellulose fibers, i.e., cellulose nanofibers (hereinafter also referred to as CNF) can be obtained by repeatedly subjecting wood cellulose to mechanical treatment using a blender or a grinder. It has been reported that the CNF obtained by this method has a minor axis diameter of 10 to 50 nm and a major axis diameter of 1 μm to 10 mm. This CNF has strength five or more times larger than that of steel with one-fifth the weight, and has a very high specific surface area of 250 $m^2$/g or more; thus, the CNF is expected to be used as a resin-reinforcing filler or an adsorbent.

Further, attempts have been actively made to produce CNF by chemically treating cellulose fibers in wood in advance so as to easily micronize them, and then micronizing them by a low-energy mechanical treatment, such as a household mixer. The method of the above chemical treatment is not particularly limited, but is preferably a method of introducing anionic functional groups into cellulose fibers to facilitate micronization. Introduction of anionic functional groups into cellulose fibers makes it easier for the solvent to penetrate between cellulose microfibril structures due to the effect of osmotic pressure, and the energy required for micronizing the cellulose raw material can be significantly reduced. Although the method for introducing anionic functional groups is not particularly limited, for example, NPL 1 discloses a method of selectively phosphorylating the surface of micronized cellulose fibers. Further, PTL 4 discloses a method of carrying out carboxymethylation by reacting cellulose with monochloroacetic acid or sodium monochloroacetate in a highly concentrated aqueous alkaline solution. Alternatively, the cellulose may be allowed to directly react with a carboxylic acid anhydride-based compound such as maleic acid, phthalic acid, or the like gasified in an autoclave to introduce carboxyl groups.

Further, there is also a report on a method of selectively oxidizing the surface of cellulose microfibers using 2,2,6,6-tetramethylpiperidinyl-1-oxy radical (TEMPO), which is a relatively stable N-oxyl compound, as a catalyst (see, for example, PTL 5). The oxidation reaction using TEMPO as a catalyst (TEMPO oxidation reaction) is capable of environmentally friendly chemical modification that progresses in an aqueous system at room temperature and atmospheric pressure. When the TEMPO oxidation reaction is applied to cellulose from wood, the reaction does not progress inside the crystal, and only the alcoholic primary carbon of a cellulose molecular chain of the surface of the crystal can be selectively converted into a carboxyl group.

Due to the osmotic effect associated with ionization of carboxyl groups selectively introduced onto the crystal surface by TEMPO oxidation, it is possible to obtain cellulose single nanofibers (hereinafter also referred to as CSNF, TEMPO-oxidized cellulose nanofiber, or TEMPO-oxidized CNF) from each cellulose microfibril unit dispersed in a solvent. CSNF shows high dispersion stability derived from the carboxyl groups on the surface thereof. It is reported that wood-derived CSNF that can be obtained from wood by the TEMPO oxidation reaction has a structure having a high aspect ratio where the minor axis diameter is about 3 nm, and the major axis diameter is several tens of nm to several tens of µm, and that its water dispersion and molded products have high transparency. PTL 6 also reports that a laminated film obtained by applying a CSNF dispersion and drying it has gas barrier properties.

Here, in order to put CNF into practical use, the problem is that the solid content concentration of the obtained CNF dispersion is as low as about 0.1 to 5%. For example, transportation of CNF dispersions is equivalent to transportation of large amounts of solvents, which causes an increase in transportation costs and significantly damages business potential. Further, in the case of use as a resin-reinforcing additive, there are problems that the addition efficiency is deteriorated due to the low solid content, and that it is difficult to form a composite when the resin is not compatible with water as a solvent. In addition, when handling a water-containing CNF dispersion, there is a risk that the CNF dispersion may e; thus, measures such as refrigeration storage and antiseptic treatment are required, which may increase costs.

However, if the solvent of the CNF dispersion is simply removed by heat drying or the like, the CNFs aggregate and keratinize, or form films, making it difficult to achieve stable behavior as an additive. Furthermore, since the solid content concentration of CNF is low, a large amount of energy is required to remove the solvent by drying, which is also a cause of damaging the business potential.

As described above, since handling CNF in a dispersion state is a cause of damaging the business potential, it is strongly desired to provide a new handling mode in which CNF can be easily handled.

On the other hand, studies have been made to add further functionality to CNF or CSNF. For example, it is possible to add further functionality using the carboxyl groups on the surface of CSNF. PTL 6 discloses a composite in which metal nanoparticles are supported on CSNF (metal nanoparticle-supported CSNF) obtained by reducing and depositing a metal in a state in which metal ions are adsorbed to the carboxyl groups on the surface of CSNF. PTL 7 discloses an example using metal nanoparticle-supported CSNF as a catalyst, and reports that catalytic activity is improved by enabling metal nanoparticles to be dispersed and stabilized in a state of high specific surface area.

As described above, various studies have been made for developing high-performance members that add new functionality to micronized cellulose, such as CNF or CSNF, which are carbon neutral materials.

There is a demand for microcapsules that encapsulate functional components in a simple manner without using additives, such as surfactants, and that have improved or even excellent dispersion stability and thus improved or even excellent sustained-release properties. Further, it is also strongly desired to provide a new handling mode in which micronized cellulose, which is an environmentally friendly material, can be easily handled.

[Citation List] [Patent Literature] PTL 1: JP H09-208494 A; PTL 2: JP 2006-1188 A; PTL 3: JP 2010-216021 A; PTL 4: WO 2014/088072; PTL 5: JP 2008-001728 A; PTL 6: WO 2013/042654; PTL 7: WO 2010/095574; PTL 8: JP 2913093 B; PTL 9: JP 2017-42617 A

[Non-Patent Literature] NPL 1: Noguchi Y, Homma I, Matsubara Y. Complete nanofibrillation of cellulose prepared by phosphorylation. Cellulose. 2017; 24:1295.10.1007/s10570-017-1191-3.

SUMMARY OF THE INVENTION

Technical Problem

The present invention has been made in view of such circumstances. An object of the present invention is to provide sustained-release composite particles having improved or even excellent dispersion stability and improved or even excellent sustained-release properties, and exhibiting long-term effects, a method for producing the sustained-release composite particles, a dry powder comprising the sustained-release composite particles, and wallpaper comprising the sustained-release composite particles.

Solution to Problem

In order to solve the above problems, the present invention proposes the following solution.

Sustained-release composite particles according to one embodiment of the present invention comprise core particles containing at least one type of polymer and at least one type of functional component, and micronized cellulose coating or shell on at least a part of the surface of the core particles, the core particles and the micronized cellulose being inseparable from each other.

A method for producing sustained-release composite particles according to one embodiment of the present invention comprises: a step a1 of defibrating a cellulose raw material in a solvent to obtain a dispersion of micronized cellulose; a step a2 of preparing a monomer mixture containing at least one type of polymerizable monomer and at least one type of functional component; a step a3 of coating, with the micronized cellulose, at least a part of the surface of polymerizable monomer droplets composed of the monomer mixture containing the polymerizable monomer and the functional component in the dispersion of the micronized cellulose to stabilize the polymerizable monomer droplets as an emulsion; and a step a4 of polymerizing the polymerizable monomer droplets in a state in which at least a part of the surface of the polymerizable monomer droplets is coated with the micronized cellulose to form core particles containing a polymer and the functional component, thereby coating at least a part of the surface of the core particles with the micronized cellulose, and making the core particles and the micronized cellulose inseparable from each other.

A method for producing sustained-release composite particles according to another embodiment of the present invention comprises step b1 of fibrillating a cellulose raw material in a solvent to obtain a dispersion of micronized cellulose; step b2 of preparing a polymer solution by adding and dissolving at least one type of polymer and at least one type of functional component in an organic solvent in which the polymer is soluble; step b3 of coating, with the micronized cellulose, at least a part of the surface of polymer droplets composed of the polymer solution containing the polymer, the functional component, and the organic solvent in the dispersion of the micronized cellulose to stabilize the polymer droplets as an emulsion; and step b4 of removing the organic solvent contained with the polymer droplets to solidify the polymer in a state in which at least a part of the surface of the polymer droplets is coated with the micronized cellulose to form core particles containing the polymer and the functional component, thereby coating at least a part of the surface of the core particles with the micronized cellulose, and making the core particles and the micronized cellulose inseparable from each other.

A dry powder according to one embodiment of the present invention comprises the sustained-release composite particles described above.

Wallpaper according to another embodiment of the present invention comprises the sustained-release composite particles described above.

Advantageous Effects of the Invention

According to one embodiment of the composite particles of the present invention, it is possible to provide sustained-release composite particles having improved or even excellent dispersion stability and thus improved or even excellent sustained-release properties, and exhibiting long-term effects, a method for producing the sustained-release composite particles, a dry powder comprising the sustained-release composite particles, and wallpaper comprising the sustained-release composite particles.

DETAILED DESCRIPTION

Description of Embodiments

Figure 1:
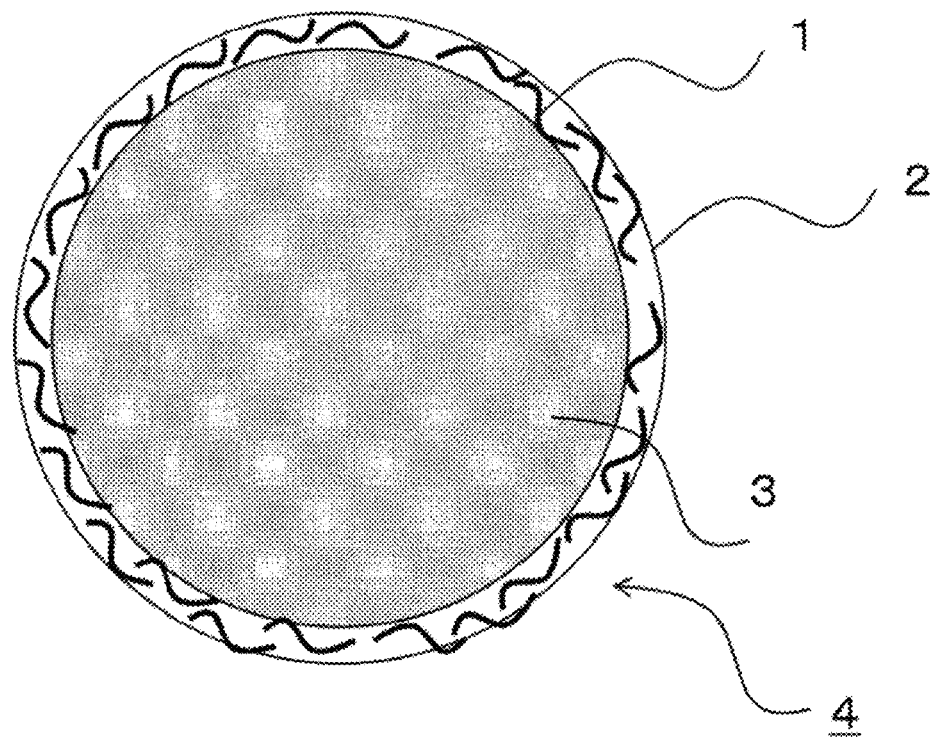
FIG. 1 is a schematic diagram of a micronized cellulose sustained-release composite particle according to first and second embodiments of the present invention.

Each embodiment of the present invention will be described below with reference to the drawings. However, in each of the drawings explained below, the same reference numerals are given to portions corresponding to each other, and explanation thereof will be omitted as appropriate for redundant portions. The present embodiments exemplify a configuration for embodying the technical idea of the present invention, and are not intended to limit the material, shape, structure, arrangement, size, and the like of each component to those set out below. The technical idea of the present invention may be altered in various manners within the scope of the claims.

First Embodiment

<Sustained-Release Composite Particles>

First, the sustained-release composite particles 4 according to the first embodiment of the present invention will be described.

FIG. 1 is a schematic view of the sustained-release composite particles (hereinafter also referred to as composite particles) 4 that have a coating or shell layer 2 composed of micronized cellulose (hereinafter also referred to as cellulose nanofibers or CNF) 1 on the surface of core particles 3 containing a polymer and a functional component. The term "micronized cellulose" as used herein refers to fibrous cellulose having a number average minor axis diameter within a range of 1 nm or more and 1000 nm or less. For purposes of this invention, the use of the terms "coating" and "shell" have the same meaning.

The composite particles 4 comprise core particles 3 containing at least one type of polymer and at least one type of functional component, and a coating layer 2 composed of micronized cellulose 1 and coating at least a part of the surface of the core particles 3, the core particles 3 and the micronized cellulose 1 being bonded and inseparable from each other.

The method for producing the composite particles 4 is not particularly limited, and a known method can be used. Examples thereof include polymerization granulation methods in which particles are formed in the polymerization process from polymerizable monomers (an emulsion polymerization method, a suspension polymerization method, a seed polymerization method, a radiation polymerization method, etc.), and dispersion granulation methods in which particles are formed from polymer solutions formed into microdroplets (a spray drying method, an in-liquid curing method, a solvent evaporation method, a phase separation method, a solvent dispersion cooling method, etc.).

Although it is not particularly limited, for example, an O/W Pickering emulsion may be formed using micronized cellulose 1, and droplets inside the emulsion are solidified to form solid core particles 3, whereby composite particles 4 in which the core particles 3 and the micronized cellulose 1 are bonded and inseparable from each other can be obtained. The use of the micronized cellulose 1 makes it possible to form droplets without using additives, such as surfactants, and composite particles 4 with high dispersibility can be obtained. The method of solidifying the droplets is not particularly limited. For example, solidification can be achieved by a known method, such as a method of polymerizing a monomer, a method of solidifying a polymer, or a method of evaporating the solvent of a polymer solution.

Figure 2:
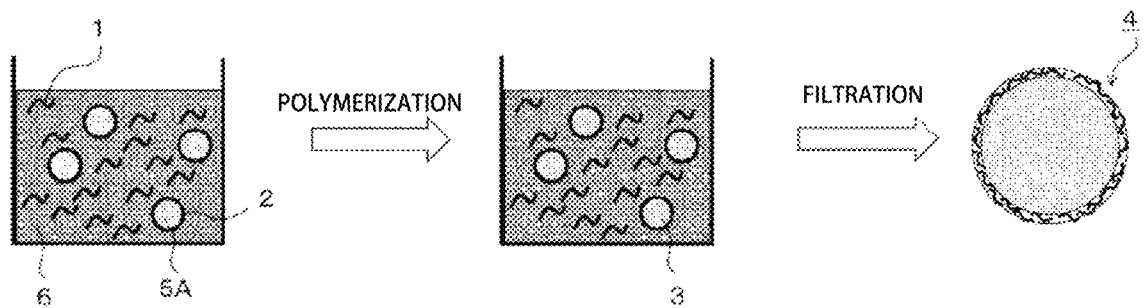
FIG. 2 shows a schematic diagram of a method for producing composite particles by using an O/W Pickering emulsion using micronized cellulose, and polymerizing a monomer inside the emulsion, according to the first and second embodiments of the present invention.
Figure 3:
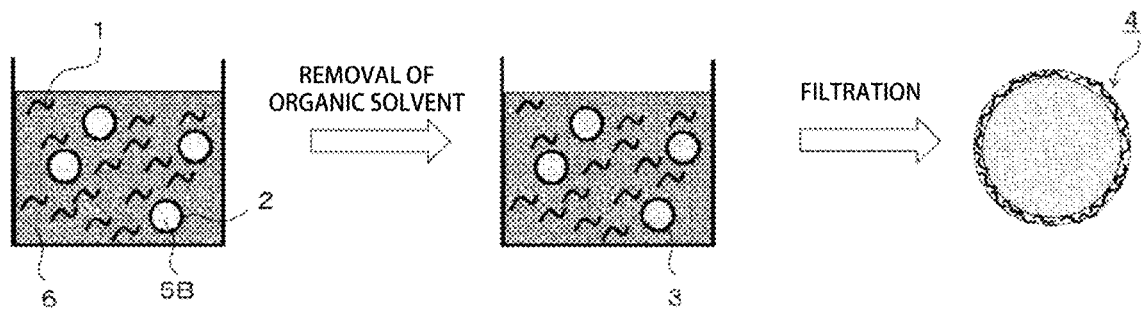
FIG. 3 shows a schematic diagram of a method for producing composite particles by using an O/W Pickering emulsion using micronized cellulose, and removing an organic solvent from the emulsion to solidify a polymer, according to the first embodiment of the present invention.

FIGS. 2 and 3 show examples of the method for producing sustained-release composite particles 4 according to the first embodiment of the present invention.

FIG. 2 shows an example of the method for producing composite particles 4 obtained by using an O/W Pickering emulsion using micronized cellulose 1, and polymerizing a polymerizable monomer inside the emulsion. As shown in FIG. 2, cellulose 1 is adsorbed to at least a part of the interface of polymerizable monomer droplets 5A (hereinafter also referred to as droplets 5A) containing a polymerizable monomer and a functional component dispersed in water 6, which is a dispersion, thereby stabilizing the O/W Pickering emulsion. The polymerizable monomer inside the emulsion is polymerized while maintaining a stabilized state, thereby producing composite particles 4 using the emulsion as a template.

FIG. 3 shows an example of the method for producing sustained-release composite particles 4 obtained by using an O/W Pickering emulsion using micronized cellulose 1, and removing an organic solvent from polymer droplets 5B (hereinafter also referred to as droplets 5B) in which a polymer is dissolved in the organic solvent inside the emulsion. As shown in FIG. 3, the micronized cellulose 1 is adsorbed to the interface of the droplets 5B containing an organic solvent, a polymer, and a functional component dispersed in water 6, thereby stabilizing the O/W Pickering emulsion. The polymer inside the emulsion is solidified while maintaining a stabilized state, thereby producing composite particles 4 using the emulsion as a template.

The term "inseparable" as used herein means that the micronized cellulose 1 and the core particles 3 are not separated from each other, and the coating of the core particles 3 with the micronized cellulose 1 is maintained, for example, even after repeating the operation of centrifuging a dispersion containing composite particles 4 to remove the supernatant, and purifying and washing the composite particles 4 by redispersing them in a solvent, or the operation of repeatedly washing them with a solvent by filtration washing using a membrane filter. The coating state can be confirmed, for example, by observing the surface of the composite particles 4 with a scanning electron microscope. Although the mechanism of binding between the micronized cellulose 1 and the core particles 3 in the composite particles 4 is not clear, the composite particles 4 are formed using an O/W emulsion stabilized by the micronized cellulose 1 as a template, and are thus solidified as the core particles 3 by polymerization of the monomer etc., while the micronized cellulose 1 is in contact with droplets 5 inside the emulsion; therefore, it is expected that in the composite particles 4 obtained after solidification, at least a part of the micronized cellulose 1 present on the surface of the core particles 3 is disposed inside the core particles 3. For this reason, it is presumed that the micronized cellulose 1 is physically fixed to the surface of the core particles 3, and that the core particles 3 and the micronized cellulose 1 are finally made inseparable from each other.

Here, the O/W emulsion is also referred to as an oil-in-water emulsion, in which oil is dispersed as oil droplets (oil particles) in water, which is a continuous phase.

Although it is not particularly limited, when composite particles 4 are produced using, as a template, an O/W emulsion stabilized by micronized cellulose 1, the composite particles 4 have a spherical shape derived from the O/W emulsion. Specifically, a coating layer 2 having a relatively uniform thickness and composed of the micronized cellulose 1 is formed on the surface of the spherical core particles 3. It is sufficient that the coating layer 2 coats at least a part of the surface of the core particles 3.

The average particle size of the composite particles 4 can be confirmed, for example, by observation with an optical microscope. Specifically, the average particle size can be calculated by randomly measuring the particle size of 100 composite particles 4, and taking the average value of the diameters of the composite particles 4. The average particle size is not particularly limited, but is preferably 0.1 µm or more and 1000 µm or less. If the average particle size of the composite particles 4 is less than 0.1 µm, it may be difficult to maintain the sustained-release properties for a long period of time. Moreover, if the average particle size of the composite particles 4 exceeds 1000 µm, it may be difficult to handle the composite particles 4. The thickness of the coating layer 2 composed of the micronized cellulose 1 is not particularly limited; however, when the thickness of the coating layer 2 is 3 nm or more and 1000 nm or less, the sustained-release properties tend to be easily controlled. The sustained-release properties can be controlled by the ratio and particle size of the functional component contained in the core particles 3, and the thickness of the coating layer 2.

The average thickness of the coating layer 2 can be measured, for example, by cutting the composite particles 4 fixed in an embedding resin using a microtome, observing it with a scanning electron microscope, measuring the thickness of the coating layer 2 in the cross-sectional image of the composite particles 4 at 100 random locations on the image, and taking the average value thereof.

Further, the composite particles 4 are characterized in that they are uniformly coated with the coating layer 2 having a relatively uniform thickness. Specifically, the coefficient of variation of the thickness of the coating layer 2 is preferably 0.5 or less, and more preferably 0.4 or less. If the coefficient of variation of the thickness of the coating layer 2 containing the micronized cellulose 1 exceeds 0.5, for example, it may be difficult to control the sustained-release properties of the composite particles 4, and to collect the composite particles 4.

Although the micronized cellulose 1 of the present embodiment is not particularly limited, for example, at least a part of the micronized cellulose 1 is preferably crystallized, and the crystal surface of the micronized cellulose 1 has anionic functional groups. The anionic functional group content is preferably 0.1 mmol or more and 5.0 mmol or less per 1 g of cellulose. If the anionic functional group content is less than 0.1 mmol per 1 g of cellulose, for example, it is difficult to control the particle size of the composite particles 4, the particle size distribution may be broadened, and the dispersibility of the micronized cellulose 1 in water (dispersion) 6 may be reduced. Moreover, if the anionic functional group content exceeds 5.0 mmol per 1 g of cellulose, for example, the adsorption stability of the micronized cellulose 1 to the droplets 5 is lowered; as a result, the micronized cellulose 1 may be less likely to be fixed to the core particles 3, and the thickness of the coating layer 2 may not be uniform.

Further, the micronized cellulose 1 preferably has a fiber form derived from a microfibril structure. Specifically, it is preferable that the micronized cellulose 1 is fibrous, and has a number average minor axis diameter of 1 nm or more and 1000 nm or less, and a number average major axis diameter of 50 nm or more; and that the number average major axis diameter is 5 or more times longer than the number average minor axis diameter. In addition, the crystal structure of the micronized cellulose 1 is preferably cellulose type I.

The core particles 3 contain at least one type of polymer and at least one type of functional component. The polymer may be a known polymer, or may be a polymer obtained by polymerizing a polymerizable monomer by a known method.

Examples of the polymer include, but are not particularly limited to, acrylic-based polymers, epoxy-based polymers, polyester-based polymers, amino-based polymers, silicone-based polymers, fluorine-based polymers, urethane/isocyanate-based polymers, and the like.

Although it is not particularly limited, the polymer is preferably a biodegradable polymer. The term "biodegradable" as used herein means a polymer that is decomposed and disappears in the global environment, such as in soil and seawater, or/and a polymer that is decomposed and disappears in the living body. In general, polymers are decomposed in soil and seawater by enzymes possessed by microorganisms, whereas polymers are decomposed in the living body by physicochemical hydrolysis, without the need to use enzymes.

Biodegradable polymers include naturally occurring natural polymers and synthetic polymers. Examples of natural polymers include polysaccharides produced by plants (e.g., cellulose, starch, and alginic acid), polysaccharides produced by animals (e.g., chitin, chitosan, and hyaluronic acid), proteins (e.g., collagen, gelatin, and albumin), and polyesters produced by microorganisms (poly(3-hydroxyalkanoate)), polysaccharides (e.g., hyaluronic acid), and the like. The biodegradable polymers will be described later.

The functional component is a substance that functions by affecting organisms, such as animals, plants, and fungi. Example thereof include, but are not particularly limited to, antifungal agents, perfumes, fertilizers (biological fertilizers, chemical fertilizers, organic fertilizers, etc.), pH adjusting agents, pesticides (insecticides, fungicides, herbicides, etc.), plant activators, plant life extenders, pest and animal repellents, soil penetrants, nutritional components (minerals, etc.), plant hormones, inorganic particles (titanium oxide, silica, clay, etc.), antibacterial substances, and the like.

These functional components may be used in the environment, such as with plants and soil, and the use of the sustained-release composite particles 4 of the present embodiment makes it possible to reduce the amounts of functional components used, and to reduce the environmental load. Particularly preferable functional components are antifungal agents, perfumes, fertilizers (biological fertilizers, chemical fertilizers, organic fertilizers, etc.), pH adjusting agents, pesticides, plant activators, plant life extenders, pest and animal repellents, soil penetrants, nutrient components, plant hormones, and antibacterial substances.

Examples of pesticides include insecticides, fungicides, herbicides, rodenticides, plant growth regulators, attractants, repellents, and the like.

Examples of insecticides include azoxybenzene, anabasine, aramite, aldrin, allethrin, isoxathion, isothioate, ethion, ethylthiomethon, endrin, ortho-dichlorobenzene, carbam, cartap, calvinphos, chloropicrin, chlorpyrifos, chlorophenamidine, chloropropylate, chlorobenzilate, chloromethane sulfonamide, sodium fluorosilicate, kelthane, salithion, ethylene oxide, propylene oxide, dialifol, dioxacarb, dimethoate, methyl bromide, tricyclohexyltin hydroxide, terbam, diazinon, thiometon, tetradifon, telodrine, vamidothion, arsenic acid lime, lead arsenate, proclonol, propaphos, promecarb, benzoepin, benzomate, phosalone, formothion, mecarbam, methomyl, metaldehyde, methyl demeton, menazon, methyl iodide, zinc phosphide, aluminum phosphide, APC, DDVP, MEP, PMP, and the like.

Examples of fungicide include amobam, sulfur, echlomezol, triphenyltin chloride, tripropyltin chloride, nickel chloride, benzalkonium chloride, basic copper chloride, basic copper sulfate, captan, guanidine, griseofulvin, chloramphenicol, triphenyltin acetate, tributyltin acetate, nickel acetate, sodium hypochlorite, dichlozoline, cycloheximide, dichlone, dithianon, zineb, dimethylamobam, ziram, triphenyltin hydroxide, streptomycin, cellocidin, difolatan, thiadiazine, thiabendazole, thiophanate, thiophanate methyl, triazine, nitrostyrene, novobiocin, validamycin, hydroxyisoxazole, ferbam, folpet, propykel, propineb, benomyl, polyoxin, polycarbamate, formaldehyde, manzeb, maneb, methylam, MAF, PCP, and the like.

Examples of herbicides include ioxynil, aziprotryn, asulam, atrazine, ametrine, alachlor, sodium ethylxanthate, calcium chlorate, sodium chlorate, oxadiazon, credazine, chlothizole, chlomethoxynil, sodium cyanate, diquat, siduron, diphenamide, cimetrin, ammonium sulfamate, terbacil, desmethrin, tetrapion, triethazine, trifluralin, nitralin, vernolate, percolate, picloram, phenothiol, phenmedipham, butachlor, propyzamide, bromacil, prometryn, bethrodine, pebulate, molinate, linuron, copper sulfate, lenacil, ACN, DBN, and the like.

Examples of rodenticides include ANTU, yellow phosphorus, chlorophacinone, thallium acetate, scilliroside, thiosemicarbazide, sodium monofluoroacetate, thallium sulfate, zinc phosphide, and the like.

Examples of plant growth regulators include indolebutyric acid, oxyethylene rapeseed oil alcohol, ortho-nitrophenol, gibberellin, α-naphthylacetamide, polybutene, maleic acid hydrazide, α-methoxymethylnaphthalene, oxyquinoline sulfate, and the like.

Examples of attractants, repellents, and the like include cue-lure, cresol, ferric oxide, diallyl disulfide, cycloheximide, quicklime, calcium carbonate, thiuram, tetrahydrothiophene, β-naphthol, methyleugenol, and the like.

Examples of fertilizers include urea, potassium sulfate, potassium phosphate, potassium chloride, ammonium sulfate, ammonium phosphate, ammonium nitrate, ammonium chloride, and the like. In particular, it is preferable to use chemical slow-release fertilizers. Chemical slow-release fertilizers are mainly nitrogen fertilizers that are chemically treated to suppress their solubility. Chemical slow-release fertilizers are difficult to dissolve in water and are slowly converted to inorganic nitrogen in soil to exert a fertilizer effect. Therefore, when the composite particles 4 encapsulate a chemical slow-release fertilizer, the fertilizing effect thereof can be further controlled.

Examples of chemical slow-release fertilizers include ureaformaldehyde (UF), methylol urea, acetaldehyde-condensation urea (CDU), isobutyraldehyde-condensation urea (IB), and glyoxal-condensation urea, all of which comprise urea and aldehydes as raw materials; guanylurea sulfate comprising lime nitrogen as a raw material; and oxamide comprising oxalic acid diester and ammonia as raw materials.

The functional component may be in the form of a solid, gas, or liquid. The content ratio of the functional component in the composite particles 4 is not particularly limited, and it is preferable to increase the content ratio within a range in which the composite particles 4 can stably maintain their shape. The content ratio of the functional component is preferably 0.001 parts by mass or more and 80 parts by mass or less when the content of the composite particles 4 is 100 parts by mass. If the content ratio of the functional component is less than 0.001 parts by mass, the effect of the contained functional component is less likely to be obtained. Moreover, if the content ratio of the functional component exceeds 80 parts by mass, it tends to be difficult to form the composite particles 4.

<Method a for Producing Composite Particles 4>

An example of the method for producing composite particles 4 of the present embodiment will be described. The method for producing composite particles 4 of the present embodiment is not limited to the production method described below.

The method for producing composite particles 4 according to the present embodiment is a method for producing sustained-release composite particles, comprising: a step of defibrating a cellulosic raw material in a solvent to obtain a dispersion of micronized cellulose 1 (step a1); a step of preparing a polymerizable monomer mixture containing at least one type of polymerizable monomer and at least one type of functional component (step a2); a step of coating, with the micronized cellulose 1, at least a part of the surface of polymerizable monomer droplets 5A containing the polymerizable monomer mixture in the dispersion of the micronized cellulose 1 obtained in step a1 to stabilize the polymerizable monomer droplets 5A as an emulsion (step a3); and a step of polymerizing the polymerizable monomer in the polymerizable monomer droplets 5A to form core particles 3 containing the polymer and the functional component, whereby at least a part of the surface of the core particles 3 is coated with the micronized cellulose 1, and the core particles 3 and the micronized cellulose 1 are made inseparable from each other (step a4).

The composite particles 4 obtained by the above production method are obtained as a dispersion in a solvent. Further, the composite particles 4 are obtained as a dry solid by removing the solvent. The method for removing the solvent is not particularly limited. For example, the composite particles 4 can be obtained as a dry solid by removing excess water by a centrifugal separation method or a filtration method, further followed by heat-drying in an oven. In this case, the obtained dry solid is not in the form of a film or aggregate, but is obtained as a fine powder. Although the reason for this is not clear, it is generally known that when the solvent is removed from the micronized cellulose 1 dispersion, the micronized cellulose 1 strongly aggregates to form a film. On the other hand, in the case of a dispersion containing composite particles 4, due to the spherical composite particles 4 in which micronized cellulose 1 is fixed to surfaces thereof, the micronized cellulose 1 does not aggregate even when removing the solvent, and is only in point contact with the composite particles 4; thus, it is considered that the dry solid is obtained as a fine powder. In addition, since there is no aggregation of the composite particles 4, the composite particles 4 obtained as a dry powder can be easily redispersed in a solvent again, and even after redispersion, they show dispersion stability derived from micronized cellulose 1 bonded to the surface of the composite particles 4.

The dry powder of the composite particles 4 is a dry solid characterized by containing almost no solvent and being redispersible in solvents. Specifically, the solid content can be set to 80% or more, more preferably 90% or more, and still more preferably 95% or more. Since the solvent can be almost completely removed, preferable effects are obtained from the viewpoints of, for example, reduction of transportation costs, prevention of decay, improvement of addition rate, and improvement of kneading efficiency for resins. When the solid content is set to 80% or more by drying treatment, the micronized cellulose 1 easily absorbs moisture, so that moisture in the air may be adsorbed, and the solid content may decrease with time. However, in consideration of the technical idea of the present invention characterized in that composite particles 4 can be easily obtained as a dry powder and can be further redispersed, it is defined that dry solids produced by a method for producing dry solids comprising the step of setting the solid content of a dry powder containing composite particles 4 to 80% or more are included in the technical scope of the present invention.

Hereinafter, each of the steps will be described in detail.
(Step a1)

Step a1 is a step of fibrillating a cellulose raw material in a solvent to obtain a micronized cellulose dispersion. First, various cellulose raw materials are dispersed in a solvent to prepare a suspension. The concentration of the cellulose raw material in the suspension is preferably 0.1% or more and less than 10%. It is not preferable that the concentration of the cellulose raw material in the suspension is less than 0.1%, because the amount of the solvent is excessive, which tends to impair the productivity. It is also not preferable that the concentration of the cellulose raw material in the suspension is 10% or more, because the suspension rapidly thickens following the fibrillation of the cellulose raw material, which tends to make uniform fibrillation treatment difficult. The solvent used for preparing the suspension preferably contains 50% or more of water. If the water content of the suspension is less than 50%, dispersion of the micronized cellulose 1 tends to be inhibited in the step of fibrillating a cellulose raw material in a solvent to obtain a micronized cellulose dispersion, described later. Further, the solvent contained in addition to water is preferably a hydrophilic solvent. Although the hydrophilic solvent is not particularly limited, preferable examples thereof include alcohols, such as methanol, ethanol, and isopropanol; cyclic ethers, such as tetrahydrofuran; and the like. If necessary, in order to increase the dispersibility of cellulose and the micronized cellulose 1 to be produced, the pH of the suspension may be adjusted, for example. Examples of the alkaline aqueous solution used for pH adjustment include organic alkalis, such as sodium hydroxide aqueous solution, lithium hydroxide aqueous solution, potassium hydroxide aqueous solution, ammonia aqueous solution, tetramethylammonium hydroxide aqueous solution, tetraethylammonium hydroxide aqueous solution, tetrabutylammonium hydroxide aqueous solution, and a benzyltrimethylammonium hydroxide aqueous solution. A sodium hydroxide aqueous solution is preferable from the viewpoints of cost and the like.

Next, the suspension is subject to physical fibrillation treatment to micronize the cellulose raw material. The method of physical fibrillation is not particularly limited, and examples thereof include mechanical treatment using a high-pressure homogenizer, an ultrahigh-pressure homogenizer, a ball mill, a roll mill, a cutter mill, a planetary mill, a jet mill, an attritor, a grinder, a juicer mixer, a homomixer, an ultrasonic homogenizer, a nanogenizer, or aqueous counter collision. By carrying out such physical fibrillation treatment, the cellulose in the suspension can be micronized, thereby obtaining a dispersion of cellulose (micronized cellulose) 1 that is micronized until at least one side of the structure thereof becomes nanometer-order in length. Further, the number average minor axis diameter and number average major axis diameter of the obtained micronized cellulose 1 can be adjusted depending on the time and the number of times of the physical fibrillation treatment.

As described above, a dispersion of cellulose 1 (micronized cellulose dispersion) is obtained in which the cellulose is micronized until at least one side of the structure thereof becomes nanometer-order in length. The obtained dispersion can be used as a stabilizer for an O/W emulsion, described later, as it is or after dilution, concentration, or the like.

In addition, the dispersion of the micronized cellulose 1 may contain, if necessary, other components other than cellulose and the components used for pH adjustment, to the extent that the effects of the present invention are not impaired. The other components are not particularly limited, and can be suitably selected from known additives according to the application etc. of the composite particles 4. Specific examples thereof include organometallic compounds, such as alkoxysilanes, or hydrolysates thereof, inorganic layered compounds, inorganic acicular minerals, antifoaming agents, inorganic particles, organic particles, lubricants, antioxidants, antistatic agents, ultraviolet absorbers, stabilizers, magnetic powders, orientation promoters, plasticizers, crosslinking agents, magnetic substances, drugs, pesticides, perfumes, adhesives, enzymes, pigments, dyes, deodorants, metals, metal oxides, inorganic oxides, and the like.

Since the micronized cellulose 1 generally has a fiber form derived from a microfibril structure, the micronized cellulose 1 used in the production method of the present embodiment preferably has a fiber form within the range shown below. That is, the form of the micronized cellulose 1 is preferably fibrous. In addition, the fibrous micronized cellulose 1 may have a number average minor axis diameter of 1 nm or more and 1000 nm or less, and preferably 2 nm or more and 500 nm or less. If the number average minor axis diameter is less than 1 nm, a highly crystalline and rigid micronized cellulose 1 fiber structure cannot be formed, and it tends to be difficult to stabilize the emulsion and to form composite particles 4 by the polymerization reaction using the emulsion as a template and the solidification of the polymer. On the other hand, if the number average minor axis diameter exceeds 1000 nm, the size becomes too large to stabilize the emulsion; thus, it tends to be difficult to control the size and form of the resulting composite particles 4. The number average major axis diameter is not particularly limited, but may be preferably 5 or more times longer than the number average minor axis diameter. It is not preferable that the number average major axis diameter is less than 5 times longer than the number average minor axis diameter, because it tends to be difficult to sufficiently control the size and form of the composite particles 4.

The number average minor axis diameter of the micronized cellulose 1 is obtained as the average value of the minor axis diameters (minimum diameters) of 100 fibers measured by observation with a transmission electron microscope or an atomic force microscope. Also, the number average major axis diameter of the micronized cellulose 1 is obtained as the average value of the major axis diameters (maximum diameters) of 100 fibers measured by observation with a transmission electron microscope or an atomic force microscope.

The type and crystal structure of cellulose that can be used as a raw material for the micronized cellulose 1 are not particularly limited. Specifically, as a raw material composed of cellulose I type crystals, for example, in addition to wood-based native cellulose, non-wood-based native cellulose can be used such as cotton linters, bamboo, hemp, bagasse, kenaf, bacterial cellulose, tunicate cellulose, and valonia cellulose. Furthermore, regenerated cellulose represented by a rayon fiber and a cuprammonium rayon fiber composed of cellulose II type crystals can also be used. In view of ease of the acquisition of the material, wood-based native cellulose is preferably used as the raw material. Examples of materials that can be used as wood-based native cellulose include, but are not particularly limited to, materials typically used for producing cellulose nanofibers, such as softwood pulp, hardwood pulp, and waste paper pulp. Softwood pulp is preferable because it is easily purified and micronized.

Further, the micronized cellulose raw material is preferably chemically modified. More specifically, it is preferable that anionic functional groups are introduced into the crystal surface of the micronized cellulose raw material. This is because the introduction of anionic functional groups into the cellulose crystal surface facilitates infiltration of the solvent between the cellulose crystals due to the osmotic effect, and facilitates micronization of the cellulose raw material.

Although the type of anionic functional group introduced into the cellulose crystal surface, and the introduction method thereof are not particularly limited, carboxyl groups and phosphate groups are preferably used. Carboxyl groups are preferable because they can be easily selectively introduced into the cellulose crystal surface.

The method for introducing carboxyl groups into the surface of the cellulose fibers is not particularly limited. Specifically, for example, carboxymethylation may be carried out by reacting cellulose with monochloroacetic acid or sodium monochloroacetate in a highly concentrated aqueous alkaline solution. Alternatively, the cellulose may be allowed to directly react with a carboxylic acid anhydride-based compound such as maleic acid, phthalic acid, or the like gasified in an autoclave to introduce carboxyl groups. Alternatively, a process may be used which uses a co-oxidant in the presence of an N-oxyl compound such as TEMPO, which has high selectivity with respect to the oxidation of alcoholic primary carbon, while the structure is retained as much as possible in a relatively mild aqueous system. Oxidation using an N-oxyl compound is more preferable for the selectivity of the site for introducing carboxyl groups and the reduction of environmental load.

Examples of N-oxyl compounds include TEMPO (2,2,6,6-tetramethylpiperidine-1-oxy radical), 2,2,6,6-tetramethyl-4-hydroxypiperidine-1-oxyl, 4-methoxy-2,2,6,6-tetramethylpiperidine-N-oxyl, 4-ethoxy-2,2,6,6-tetramethylpiperidine-N-oxyl, 4-acetamide-2,2,6,6-tetramethylpiperidine-N-oxyl, and the like. Among these, TEMPO, which has high reactivity, is preferable. The amount of N-oxyl compound used may be a catalytic amount and is not particularly limited. Typically, the amount is approximately 0.01 to 5.0% by mass with respect to the solid content of the wood-based native cellulose subject to the oxidation treatment.

Examples of the oxidation method using an N-oxyl compound include a method of dispersing wood-based native cellulose in water, and oxidizing the cellulose in the presence of the N-oxyl compound. In this method, a co-oxidant is preferably used together with the N-oxyl compound. In this case, in the reaction system, the N-oxyl compound is gradually oxidized by the co-oxidant to generate an oxoammonium salt, by which the cellulose is oxidized. According to this oxidation treatment, the oxidation reaction proceeds smoothly even under mild conditions, whereby the efficiency of introducing carboxyl groups is improved. When the oxidation treatment is carried out under mild conditions, the crystal structure of the cellulose can be easily maintained.

As the co-oxidant, any oxidant, such as halogen, hypohalous acid, halous acid, perhalogenic acid, salts thereof, halogen oxide, nitrogen oxide, and peroxide, can be used, as long as they can accelerate the oxidation reaction. From the viewpoints of availability and reactivity, sodium hypochlorite is preferable. The amount of the co-oxidant to be used is not particularly limited as long as it can accelerate the oxidation reaction. Typically, the amount is approximately 1 to 200% by mass with respect to the solid content of the wood-based native cellulose subjected to the oxidation treatment.

In addition, together with the N-oxyl compound and the co-oxidant, at least one compound selected from the group consisting of bromide and iodide may be used in combination. Hence, the oxidation reaction can proceed smoothly, whereby the efficiency of introducing carboxyl groups can be improved. As such a compound, sodium bromide or lithium bromide is preferable, and sodium bromide is more preferable from the viewpoints of cost and stability. The amount of the compound to be used is not particularly limited as long as it can accelerate the oxidation reaction.

Typically, the amount is approximately 1 to 50% by mass with respect to the solid content of the wood-based native cellulose subjected to the oxidation treatment.

The reaction temperature of the oxidation reaction is preferably 4° C. or more and 80° C. or less, and more preferably 10° C. or more and 70° C. or less. If the reaction temperature of the oxidation reaction is less than 4° C., the reactivity of the reagent tends to be lowered, thereby lengthening the reaction time. If the reaction temperature of the oxidation reaction exceeds 80° C., side reactions are promoted to reduce the molecular weight of the sample cellulose, the highly crystalline and rigid micronized cellulose 1 fiber structure is deteriorated, and it tends to be difficult to use it as a stabilizer for the O/W emulsion.

In addition, the reaction time of the oxidation treatment can be suitably set in consideration of the reaction temperature, the desired amount of carboxyl groups, and the like. The reaction time is not particularly limited, but is typically about 10 minutes to 5 hours.

The pH of the reaction system during the oxidation reaction is not particularly limited, but is preferably 9 to 11. The reaction can efficiently proceed when the pH is 9 or higher. If the pH is higher than 11, side reactions are accelerated, which may promote the decomposition of the sample. In addition, in the oxidation treatment, as the oxidation proceeds, the pH in the system lowers due to the generation of carboxyl groups. Hence, it is preferable to keep the pH of the reaction system at 9 to 11 during the oxidation treatment. Examples of the method for keeping the pH of the reaction system at 9 to 11 include a method of adding an alkaline aqueous solution depending on the lowering of the pH.

Examples of the alkaline aqueous solution include organic alkalis, such as a sodium hydroxide aqueous solution, a lithium hydroxide aqueous solution, a potassium hydroxide aqueous solution, an ammonia aqueous solution, a tetramethylammonium hydroxide aqueous solution, a tetraethylammonium hydroxide aqueous solution, a tetrabutylammonium hydroxide aqueous solution, and a benzyltrimethylammonium hydroxide aqueous solution. A sodium hydroxide aqueous solution is preferable from the viewpoints of cost and the like.

The oxidation reaction using an N-oxyl compound can be stopped, for example, by adding an alcohol to the reaction system. In this case, the pH of the reaction system is preferably kept within the above range. As the alcohol to be added, a low-molecular-weight alcohol, such as methanol, ethanol, or propanol, is preferable because the reaction is quickly stopped. Ethanol is particularly preferable from the viewpoint of safety of by-products generated by the reaction.

The reaction solution after the oxidation treatment may be directly subjected to a micronizing step; however, in order to remove the catalyst, such as the N-oxyl compound, and impurities, the oxidized cellulose contained in the reaction solution is preferably collected and washed with a cleaning liquid. The oxidized cellulose can be collected, for example, by a known method such as filtration using a glass filter or a nylon mesh having a pore diameter of 20 The cleaning liquid used for cleansing the oxidized cellulose is preferably pure water.

When the obtained TEMPO-oxidized cellulose is subjected to fibrillation treatment, TEMPO-oxidized cellulose nanofibers (hereinafter also referred to as TEMPO-oxidized CNF, cellulose single nanofibers, or CSNF) having a uniform fiber width of about 3 nm are obtained. When CSNF is used as a raw material of the micronized cellulose 1 of the composite particles 4, the particle size of the resulting O/W emulsion tends to be uniform due to its uniform structure.

As described above, CSNF used in the present embodiment can be obtained by a step of oxidizing a cellulose raw material and a step of micronizing the cellulose raw material to obtain a dispersion. In addition, the content of carboxyl groups introduced to the CSNF is preferably 0.1 mmol/g or more and 5.0 mmol/g or less, and more preferably 0.5 mmol/g or more and 2.0 mmol/g or less. If the amount of carboxyl groups is less than 0.1 mmol/g, solvent entry due to the osmotic effect does not occur between the cellulose microfibrils, and it tends to be difficult to micronize and uniformly disperse the cellulose. In addition, if the amount of carboxyl groups exceeds 5.0 mmol/g, the molecular weight of the cellulose microfibrils is lowered due to side reactions caused by chemical treatment, so that a highly crystalline and rigid micronized cellulose 1 fiber structure cannot be formed, and it tends to be difficult to use it as a stabilizer for the O/W emulsion.

(Step a2)

Step a2 is a step of preparing a polymerizable monomer mixture containing at least one type of polymerizable monomer and at least one type of functional component. Specifically, the polymerizable monomer mixture is obtained by adding and mixing a functional component with a polymerizable monomer, although it is not particularly limited thereto.

The type of polymerizable monomer that can be used in step a2 is not particularly limited as long as it is a monomer of a polymer, has a polymerizable functional group in its structure, is a liquid at room temperature, is not completely miscible with water, and can form a polymer (high-molecular-weight polymer) by the polymerization reaction. The polymerizable monomer has at least one type of polymerizable functional group. A polymerizable monomer having one functional group is also referred to as a monofunctional monomer. Further, a polymerizable monomer having two or more polymerizable functional groups is also referred to a polyfunctional monomer. The type of monomer is not particularly limited, and examples thereof include a (meth) acrylic monomer, which is a monomer having a (meth) acrylic group, and a vinyl monomer, which is a monomer having a vinyl group. It is also possible to use a polymerizable monomer having a cyclic ether structure, such as an epoxy group or an oxetane structure (e.g., ε-caprolactone).

The term "(meth)acrylate" refers to both "acrylate" and "methacrylate."

Examples of monofunctional (meth)acrylic monomers include 2-hydroxyethyl (meth)acrylate, 2-hydroxypropyl (meth)acrylate, 2-hydroxybutyl (meth)acrylate, n-butyl (meth)acrylate, isobutyl (meth)acrylate, t-butyl (meth)acrylate, glycidyl (meth)acrylate, acryloylmorpholine, N-vinylpyrrolidone, tetrahydrofurfuryl acrylate, cyclohexyl (meth)acrylate, 2-ethylhexyl (meth)acrylate, isobornyl (meth)acrylate, isodecyl (meth)acrylate, lauryl (meth)acrylate, tridecyl (meth)acrylate, cetyl (meth)acrylate, stearyl (meth)acrylate, benzyl (meth)acrylate, 2-ethoxyethyl (meth) acrylate, 3-methoxybutyl (meth)acrylate, ethyl carbitol (meth)acrylate, phosphate (meth)acrylate, ethylene-oxide-modified phosphate (meth)acrylate, phenoxy (meth)acrylate, ethylene-oxide-modified phenoxy (meth)acrylate, propylene-oxide-modified phenoxy (meth)acrylate, nonyl phenol (meth)acrylate, ethylene-oxide-modified nonyl phenol (meth)acrylate, propylene-oxide-modified nonyl phenol (meth)acrylate, methoxy diethylene glycol (meth)acrylate, methoxy polyethylene glycol (meth)acrylate, methoxy propylene glycol (meth)acrylate, 2-(meth)acryloyl oxyethyl-2- hydroxy propyl phthalate, 2-hydroxy-3-phenoxy propyl (meth)acrylate, 2-(meth)acryloyl oxyethyl hydrogen phthalate, 2-(meth)acrtyloyl oxypropyl hydrogen phthalate, 2-(meth)acryloyl oxypropyl hexahydro hydrogen phthalate, 2-(meth)acrylol oxypropyl tetrahydro hydrogen phthalate, dimethylaminoethyl (meth)acrylate, trifluoroethyl (meth)acrylate, tetrafluoropropyl (meth)acrylate, hexafluoropropyl (meth)acrylate, octafluoropropyl (meth)acrylate, and adamantine derivatives of mono(meth)acrylate, such as adamantyl acrylate which is a monovalent mono(meth)acrylate derived from 2-adamantane and adamantine diol.

Examples of bifunctional (meth)acrylic monomers include di(meth)acrylates, such as ethylene glycol di(meth)acrylate, diethylene glycol di(meth)acrylate, butanediol di(meth)acrylate, hexanediol di(meth)acrylate, nonanediol di(meth)acrylate, ethoxylated hexanediol di(meth)acrylate, propoxylated hexanediol di(meth)acrylate, polyethylene glycol di(meth)acrylate, tripropylene glycol di(meth)acrylate, polypropylene glycol di(meth)acrylate, neopentyl glycol di(meth)acrylate, ethoxylated neopentyl glycol di(meth)acrylate, tripropylene glycol di(meth)acrylate, and hydroxy pivalate neopentyl glycol di(meth)acrylate.

Examples of trifunctional or higher (meth)acrylic monomers include tri(meth)acrylates, such as trimethylolpropane tri(meth)acrylate, ethoxylated trimethylolpropane tri(meth)acrylate, propoxylated trimethylolpropane tri(meth)acrylate, tris 2-hydroxyethyl isocyanurate tri(meth)acrylate, and glycerin tri(meth)acrylate; trifunctional (meth)acrylate compounds, such as pentaerythritol tri(meth)acrylate, dipentaerythritol tri(meth)acrylate, and ditrimethylolpropane tri(meth)acrylate; trifunctional or higher polyfunctional (meth)acrylate compounds, such as pentaerythritol tetra(meth)acrylate, ditrimethylolpropane tetra(meth)acrylate, dipentaerythritol tetra(meth)acrylate, dipentaerythritol penta(meth)acrylate, ditrimethylolpropane penta(meth)acrylate, dipentaerythritol hexa(meth)acrylate, and ditrimethylolpropane hexa(meth)acrylate; and polyfunctional (meth)acrylate compounds in which a part of each of these (meth)acrylates is replaced by an alkyl group or ε-caprolactone.

Preferable examples of monofunctional vinyl-based monomers include liquids that are incompatible with water at room temperature, such as vinyl ether-based monomers, vinyl ester-based monomers, and aromatic vinyl-based monomers; and particularly styrene and styrene-based monomers.

Among monofunctional vinyl-based monomers, examples of (meth)acrylates include methyl (meth)acrylate, ethyl (meth)acrylate, butyl (meth)acrylate, t-butyl (meth)acrylate, 2-ethylhexyl (meth)acrylate, lauryl (meth)acrylate, alkyl (meth)acrylate, tridecyl (meth)acrylate, stearyl (meth)acrylate, cyclohexyl (meth)acrylate, benzyl (meth)acrylate, isobornyl (meth)acrylate, glycidyl (meth)acrylate, tetrahydrofurfuryl (meth)acrylate, allyl (meth)acrylate, diethylaminoethyl (meth)acrylate, trifluoroethyl (meth)acrylate, heptafluorodecyl (meth)acrylate, dicyclopentenyl (meth)acrylate, dicyclopentenyloxyethyl (meth)acrylate, tricyclodecanyl (meth)acrylate, and the like.

Moreover, examples of monofunctional aromatic vinyl-based monomers include styrene, α-methylstyrene, o-methylstyrene, m-methylstyrene, p-methyl styrene, ethyl styrene, isopropenyltoluene, isobutyltoluene, tert-butylstyrene, vinylnaphthalene, vinylbiphenyl, 1,1-diphenylethylene, and the like.

Examples of polyfunctional vinyl-based monomers include polyfunctional groups having an unsaturated bond, such as divinylbenzene. A liquid that is immiscible with water at room temperature is preferable.

Specific examples of polyfunctional vinyl-based monomers include (1) divinyls, such as divinylbenzene, 1,2,4-trivinylbenzene, and 1,3,5-trivinylbenzene; (2) dimethacrylates, such as ethylene glycol dimethacrylate, diethylene glycol dimethacrylate, triethylene glycol dimethacrylate, polyethylene glycol dimethacrylate, 1,3-propylene glycol dimethacrylate, 1,4-butylene glycol dimethacrylate, 1,6-hexamethylene glycol dimethacrylate, neopentyl glycol dimethacrylate, dipropylene glycol dimethacrylate, polypropylene glycol dimethacrylate, and 2,2-bis(4-methacryloxydiethoxyphenyl)propane; (3) trimethacrylates, such as trimethylolpropane trimethacrylate and trimethylolethane trimethacrylate; (4) diacrylates, such as ethylene glycol diacrylate, diethylene glycol diacrylate, triethylene glycol diacrylate, polyethylene glycol diacrylate, 1,3-dipropylene glycol diacrylate, 1,4-dibutylene glycol diacrylate, 1,6-hexylene glycol diacrylate, neopentyl glycol diacrylate, dipropylene glycol diacrylate, polypropylene glycol diacrylate, 2,2-bis(4-acryloxypropoxyphenyl)propane, and 2,2-bis(4-acryloxydiethoxyphenyl)propane; (5) triacrylates, such as trimethylolpropane triacrylate and triethylolethane triacrylate; (6) tetraacrylates, such as tetramethylolmethane tetraacrylate; and (7) others, such as tetramethylene bis(ethyl fumarate), hexamethylene bis(acrylamide), triallyl cyanurate, and triallyl isocyanurate.

Specific examples of functional styrene-based monomers include divinylbenzene, trivinylbenzene, divinyltoluene, divinylnaphthalene, divinylxylene, divinylbiphenyl, bis(vinylphenyl)methane, bis(vinylphenyl)ethane, bis(vinylphenyl)propane, bis(vinylphenyl)butane, and the like.

In addition to these, it is also possible to use a polyether resin, a polyester resin, a polyurethane resin, an epoxy resin, an alkyd resin, a spirochete resin, a polybutadiene resin, a polythiol polyene resin, or the like having at least one or more polymerizable functional groups. The material thereof is not particularly limited.

The above polymerizable monomers may be used singly or in combination of two or more.

As described above, the functional component is not particularly limited. Example thereof include antifungal agents, perfumes, fertilizers (biological fertilizers, chemical fertilizers, organic fertilizers, etc.), pH adjusting agents, pesticides (insecticides, fungicides, herbicides, etc.), plant activators, plant life extenders, pest and animal repellents, soil penetrants, nutritional components (minerals, etc.), plant hormones, inorganic particles (titanium oxide, silica, clay, etc.), antibacterial substances, and the like.

The functional component is preferably dissolved or dispersed in the polymerizable monomer described above. Because the functional component is dispersed in the polymerizable monomer, when an O/W emulsion is formed in step a3, described later, the functional component can be easily encapsulated in droplets 5A inside the emulsion particles, and composite particles 4 encapsulating the functional component can be efficiently obtained. It is also possible to increase the amount of functional component to be encapsulated.

The weight ratio of the polymerizable monomer and the functional component that can be used in step a2 is not particularly limited; however, the addition ratio is preferably large within the range in which the composite particles 4 can stably maintain their shape. The amount of the functional component is preferably 0.001 parts by mass or more and 80 parts by mass or less, more preferably 0.01 parts by mass or more and 60 parts by mass or less, and even more preferably 0.01 parts by mass or more and 40 parts by mass or less, based on 100 parts by mass of the polymerizable monomer.

Further, a polymerization initiator may be added to the polymerizable monomer. Examples of general polymerization initiators include radical initiators, such as organic peroxides and azo polymerization initiators.

Examples of organic peroxides include peroxyketal, hydroperoxide, dialkyl peroxide, diacyl peroxide, peroxycarbonate, peroxyester, and the like.

Examples of azo polymerization initiators include ADVN and AIBN.

Examples include 2,2-azobis(isobutyronitrile) (AIBN), 2,2-azobis(2-methylbutyronitrile) (AMBN), 2,2-azobis(2,4-dimethylvaleronitrile) (ADVN), 1,1-azobis(1-cyclohexanecarbonitrile) (ACHN), dimethyl-2,2-azobisisobutyrate (MAIB), 4,4-azobis(4-cyanovaleric acid) (ACVA), 1,1-azobis(1-acetoxy-1-phenylethane), 2,2-azobis(2-methylbutyramide), 2,2-azobis(4-methoxy-2,4-dimethylvaleronitrile), 2,2-azobis(2-methylamidinopropane) dihydrochloride, 2,2-azobis[2-(2-imidazolin-2-yl)propane], 2,2-azobis[2-methyl-N-(2-hydroxyethyl)propionamide], 2,2-azobis(2,4,4-trimethylpentane), 2-cyano-2-propylazoformamide, 2,2-azobis(N-butyl-2-methylpropionamide), 2,2-azobis(N-cyclohexyl-2-methylpropionamide), and the like.

When a polymerizable monomer mixture containing a polymerization initiator is used in step a2, the polymerization initiator is contained in droplets 5A inside an O/W emulsion formed in step a3, described later; thus, the polymerization reaction is likely to proceed in step a4, described later, when the monomer inside the emulsion is polymerized.

The weight ratio of the polymerizable monomer and the polymerization initiator that can be used in step a2 is not particularly limited; however, in general, the polymerization initiator is preferably 0.1 parts by mass or more relative to 100 parts by mass of the polymerizable monomer. It is not preferable that the amount of the polymerizable monomer is less than 0.1 parts by mass, because the polymerization reaction does not proceed sufficiently, and the yield of the composite particles 4 tends to decrease.

The polymerizable monomer mixture may contain a solvent. Although it is not particularly limited, it is preferable to use an organic solvent in order to stabilize the emulsion, described later, in step a3. Examples of the organic solvent contained in the polymerizable monomer mixture include toluene, xylene, ethyl acetate, butyl acetate, methyl ethyl ketone (MEK), methyl isobutyl ketone (MIBK), isophorone, cellosolve acetate, isophorone, Solvesso 100, trichlene, hexane, chloroform, dichloromethane, dichloroethane, isooctane, nonane, and the like.

The weight ratio of the polymerizable monomer and the solvent that can be used in step a2 is not particularly limited; however, the amount of the solvent is preferably 80 parts by mass or less based on 100 parts by mass of the polymerizable monomer. It is not preferable that the amount of the solvent exceeds 80 parts by mass, because the polymerization reaction does not proceed sufficiently, and the yield of the composite particles 4 tends to decrease.

(Step a3)

Step a3 is a step of coating, with the micronized cellulose 1, at least a part of the surface of droplets 5A composed of the polymerizable monomer mixture containing a polymerizable monomer and a functional component in the dispersion of the micronized cellulose 1 obtained in step a1 to stabilize the droplets 5A as an emulsion.

Specifically, in this step, the mixture obtained in step a2 is added to the dispersion of the micronized cellulose 1 obtained in step a1, and dispersed as droplets 5A in the dispersion of the micronized cellulose 1, and at least a part of the surface of the droplets 5A containing a polymerizable monomer and a functional component is coated with the micronized cellulose 1 to produce an O/W emulsion stabilized by the micronized cellulose 1.

Although the method for producing an O/W emulsion is not particularly limited, general emulsification treatments, for example, various homogenizer treatments and mechanical stirring treatments, can be used. Specific examples thereof include mechanical treatments using a high-pressure homogenizer, an ultrahigh-pressure homogenizer, a universal homogenizer, a ball mill, a roll mill, a cutter mill, a planetary mill, a jet mill, an attritor, a grinder, a juicer mixer, a homomixer, an ultrasonic homogenizer, a nanogenizer, aqueous counter collision, or a paint shaker. Moreover, a plurality of mechanical treatments may be used in combination.

For example, when an ultrasonic homogenizer is used, a polymerizable monomer is added to the dispersion of the micronized cellulose 1 obtained in step a1 to prepare a mixed solvent, and the tip of the ultrasonic homogenizer is inserted into the mixed solvent for ultrasonic treatment. The treatment conditions of the ultrasonic homogenizer are not particularly limited. For example, the frequency is generally 20 kHz or more, and the output is generally 10 W/cm$^2$ or more. The treatment time is also not particularly limited, but is generally about 10 seconds to 1 hour.

By the above ultrasonic treatment, the droplets 5A containing a polymerizable monomer and a functional component are dispersed in the dispersion of the micronized cellulose 1 to accelerate the emulsification. Further, the micronized cellulose 1 is selectively adsorbed to the liquid/liquid interface between the droplets 5A and the dispersion of the micronized cellulose 1, thereby forming a stable structure as an O/W emulsion in which the droplets 5A are coated with the micronized cellulose 1. As described above, emulsions in which solids are adsorbed and stabilized in the liquid/liquid interface are academically called "Pickering emulsions." Although the mechanism by which the micronized cellulose 1 forms Pickering emulsions is not clear, as described above, it is presumed that cellulose is amphipathic because it has a hydrophilic site derived from a hydroxyl group and a hydrophobic site derived from a hydrocarbon group in its molecular structure, and that due to the amphipathic properties, the cellulose is adsorbed to the liquid/liquid interface between the hydrophobic monomer and the hydrophilic solvent.

The O/W emulsion structure can be confirmed, for example, by observation with an optical microscope. The particle size of the O/W emulsion is not particularly limited; however, the average particle size is preferably 0.1 μm or more and 1000 μm or less. The average particle size can be calculated, for example, by randomly measuring the diameters of 100 emulsions and taking the average value thereof.

In the O/W emulsion structure, the thickness of the coating layer 2 (micronized cellulose layer) formed on the surface layer of the droplets 5A is not particularly limited, but is preferably 3 nm or more and 1000 nm or less. Although it is not particularly limited, the particle size in the emulsion structure is about the same as the particle size of the composite particles 4 obtained in step a4. The thickness of the coating layer 2 can be measured using, for example, a cryo-TEM.

The weight ratio of the dispersion of the micronized cellulose 1 and the polymerizable monomer mixture that can be used in step a3 is not particularly limited; however, the amount of the polymerizable monomer mixture is preferably 1 part by mass or more and 50 parts by mass or less based on 100 parts by mass of the micronized cellulose 1. It is not preferable that the amount of the monomer is less than 1 part by mass, because the yield of the composite particles 4 tends to decrease. It is also not preferable that the amount of the monomer exceeds 50 parts by mass, because it tends to be difficult to uniformly coat the droplets 5A with the micronized cellulose 1.

(Step a4)

Step a4 is a step of polymerizing the polymerizable monomer in the polymerizable monomer droplets 5A to form core particles 3, thereby obtaining sustained-release composite particles having the micronized cellulose coating at least a part of the surface of the core particles, wherein the core particles and the micronized cellulose are inseparable from each other.

The method for polymerizing the monomer is not particularly limited, and can be suitably selected depending on the type of polymerizable monomer and the type of polymerization initiator. Examples of the method for polymerizing the above-mentioned polymerizable monomer include a suspension polymerization method.

The specific suspension polymerization method is also not particularly limited, and a known method can be used. For example, it can be carried out by heating while stirring the O/W emulsion prepared in step a3 in which the droplets 5A containing a polymerization initiator are coated with the micronized cellulose 1 and stabilized. The stirring method is not particularly limited, and a known method can be used. Specifically, a disperser or a stirrer can be used. Alternatively, only heat treatment may be performed without stirring. Although the temperature conditions during heating can be suitably set depending on the type of polymerizable monomer and the type of polymerization initiator, the temperature is preferably 20 degrees or more and 150 degrees or less. It is not preferable that the heating temperature is lower than 20 degrees, because the polymerization reaction rate tends to decrease. It is also not preferable that the heating temperature exceeds 150 degrees, because the micronized cellulose 1 may be modified. The time for the polymerization reaction can be suitably set depending on the type of polymerizable monomer and the type of polymerization initiator, but is generally about 1 to 24 hours. Further, the polymerization reaction may be carried out by treatment with ultraviolet irradiation, which is a kind of electromagnetic waves. In addition to electromagnetic waves, particle beams, such as electron beams, may also be used.

Through the steps described above, it is possible to produce spherical composite particles 4 in which core particles 3 are coated with micronized cellulose 1.

Immediately after the completion of the polymerization reaction, a large amount of water and free micronized cellulose 1 that does not contribute to the formation of the coating layer 2 of the composite particles 4 are mixed in the dispersion of the composite particles 4. Therefore, it is necessary to collect and purify the produced composite particles 4, and washing by centrifugation or filtration washing is preferable as the collection and purification method. A known method can be used as washing by centrifugation. Specifically, the composite particles 4 are precipitated by centrifugation to remove the supernatant, and redispersed in a water/methanol mixed solvent; this operation is repeated. Finally, the residual solvent is removed from the precipitate obtained by centrifugation to collect the composite particles 4. A known method can also be used for filtration washing. For example, suction filtration with water and methanol is repeated using a PTFE membrane filter having a pore size of 0.1 μm. Finally, the residual solvent is removed from the paste remaining on the membrane filter, whereby the composite particles 4 can be collected.

The method for removing the residual solvent is not particularly limited. For example, the residual solvent can be removed by air drying or heat drying in an oven. The thus-obtained dry solid containing the composite particles 4 does not form a film or aggregates, as described above, and can be obtained as a fine powder.

<Method b for Producing Composite Particles 4>

The second method for producing composite particles 4 of the present embodiment will be described. In the following description, the components common to those already explained are given the same reference signs, and duplicate descriptions are omitted.

The method for producing composite particles 4 according to the present embodiment is a method for producing sustained-release composite particles, comprising: a step of defibrating a cellulose raw material in a solvent to obtain a dispersion of micronized cellulose 1 (step b1); a step of adding and dissolving at least one type of polymer and at least one type of functional component in an organic solvent in in which the polymer is soluble to prepare a polymer solution (step b2); a step of coating at least a part of the surface of polymer droplets 5B with the micronized cellulose 1 in the dispersion of the micronized cellulose 1 obtained in step b1 to stabilize the polymer droplets 5B as an emulsion (step b3); and a step of removing the organic solvent from the polymer droplets 5B to solidify the polymer to form core particles 3 containing the polymer and the functional component, thereby obtaining sustained-release composite particles having the micronized cellulose 1 coating at least a part of the surface of the core particles 3, wherein the core particles 3 and the micronized cellulose 1 are inseparable from each other (step b4).

Hereinafter, each of the steps will be described in detail.

(Step b1)

Step b1 is a step of fibrillating a cellulose raw material in a solvent to obtain a dispersion of micronized cellulose 1. Step b1 is the same as step a1.

(Step b2)

Step b2 is a step of adding and dissolving at least one type of polymer and at least one type of functional component in an organic solvent that can dissolve the polymer to prepare a polymer solution.

10.156 Specifically, a polymer is added to a solvent that is not completely miscible with water but is capable of dissolving the polymer, and is mixed to dissolve the polymer. A functional component is added to this polymer solution and mixed to obtain a polymer solution.

The polymer to be dissolved in the solvent in step b2 is not particularly limited, and a known polymer can be used. Examples thereof include acrylic-based polymers, epoxy-based polymers, polyester-based polymers, amino-based polymers, silicone-based polymers, fluorine-based polymers, urethane/isocyanate-based polymers, and the like.

The polymer dissolved in the solvent in step b2 is not particularly limited, but is preferably a biodegradable polymer. The term "biodegradable" as used herein means a polymer that is decomposed and disappears in the global environment, such as in soil and seawater, or/and a polymer that is decomposed and disappears in the living body. In general, polymers are decomposed in soil and seawater by enzymes possessed by microorganisms, whereas polymers are decomposed in the living body by physicochemical hydrolysis, without the need to use enzymes.

The decomposition of the polymer means that the polymer loses its morphology due to its low molecular weight or water solubility. The decomposition of the polymer is not particularly limited, but occurs, for example, by hydrolysis of the main chain, side chains, and crosslinking points, or oxidative decomposition of the main chain.

The biodegradable polymer is, for example, a naturally occurring natural polymer or a synthetic polymer.

Examples of natural polymers include polysaccharides produced by plants (e.g., cellulose, starch, and alginic acid), polysaccharides produced by animals (e.g., chitin, chitosan, and hyaluronic acid), proteins (e.g., collagen, gelatin, and albumin), and polyesters produced by microorganisms (poly (3-hydroxyalkanoate)), polysaccharides (e.g., hyaluronic acid), and the like.

Examples of synthetic polymers include aliphatic polyesters, polyols, polycarbonates, and the like.

Examples of fatty acid polyesters include glycol/dicarboxylic acid-polycondensed polyesters (polyethylene succinate, polybutylene succinate, etc.), polylactides (polyglycolic acid, polylactic acid, etc.), polylactones (β-caprolactone, ε-caprolactone, etc.), and others (polybutylene terephthalate, adipate, etc.).

Examples of polyols include polyvinyl alcohol and the like.

Examples of polycarbonates include polyester carbonate and the like.

Example of other biodegradable polymers include biodegradable synthetic polymers, such as polyanhydrides, polycyanoacrylates, polyorthoesters, and polyphosphazenes.

As the functional component, the functional components described above can be used. The functional component is not particularly limited, but is preferably dissolved or dispersed in an organic solvent. Because the functional component is dissolved and dispersed in the polymer solution, when an O/W emulsion is formed in step b3, described later, the functional component can be easily encapsulated in droplets 5B inside the emulsion particles, and composite particles 4 encapsulating the functional component can be efficiently obtained. It is also possible to increase the amount of functional component to be encapsulated, and it becomes easier to maintain the sustained-release effect.

The weight ratio of the polymer and the functional component that can be used in step b2 is not particularly limited; however, the addition ratio is preferably large within the range in which the composite particles 4 can stably maintain their shape. The amount of the functional component is preferably 0.001 parts by mass or more and 80 parts by mass or less, more preferably 0.01 parts by mass or more and 60 parts by mass or less, and even more preferably 0.01 parts by mass or more and 40 parts by mass or less, based on 100 parts by mass of the polymer.

The organic solvent is preferably a solvent that is miscible with water and can form an emulsion in step b3. Examples the solvent used in step b3 include, but are not particularly limited to, toluene, xylene, ethyl acetate, butyl acetate, methyl ethyl ketone (MEK), methyl isobutyl ketone (MIBK), isophorone, cellosolve acetate, isophorone, Solvesso 100, trichlene, hexane, chloroform, dichloromethane, dichloroethane, isooctane, nonane, and the like.

The weight ratio of the solvent and the polymer that can be used in step b2 is not particularly limited as long as the polymer can be dissolved. The weight of the polymer is preferably 0.005 parts by mass or more and 100 parts by mass or less, more preferably 0.1 parts by mass or more and 80 parts by mass or less, based on 100 parts by mass of the solvent. If the content ratio of the polymer is less than 0.005 parts by mass, it tends to be difficult to remove the organic solvent and solidify the polymer in step b4, described later, and to be difficult to form composite particles 4. Further, if the content ratio of the polymer exceeds 100 parts by mass, it tends to be difficult to dissolve the polymer.

(Step b3)

Step b3 is a step of coating at least a part of the surface of the polymer droplets 5B at least containing the polymer solution with the micronized cellulose 1 in the dispersion of the micronized cellulose 1 obtained in step b1, thereby stabilizing the polymer droplets 5B as an emulsion.

Specifically, in this step, the polymer solution obtained in step b2 is added to the dispersion of the micronized cellulose 1 obtained in step b1, the polymer solution is dispersed as polymer droplets 5B in the dispersion of the micronized cellulose 1, and at least a part of the surface of the polymer droplets 5B is coated with the micronized cellulose 1, thereby producing an O/W emulsion stabilized by the micronized cellulose 1.

The method for producing an O/W emulsion is not particularly limited, and the O/W emulsion can be produced by the method described in step a2. By the method of step a2, the droplets 5B containing a polymer and a functional component are dispersed in the dispersion of the micronized cellulose 1 to accelerate the emulsification. Further, the micronized cellulose 1 is selectively adsorbed to the liquid/liquid interface between the droplets 5B and the dispersion of the micronized cellulose 1, thereby forming an O/W Pickering emulsion structure in which the droplets 5B are coated with the micronized cellulose 1 and are stable as an O/W emulsion.

Although the mechanism by which the micronized cellulose 1 forms Pickering emulsions is not clear, as described above, it is presumed that cellulose is amphipathic because it has a hydrophilic site derived from a hydroxyl group and a hydrophobic site derived from a hydrocarbon group in its molecular structure, and that due to the amphipathic properties, the cellulose is adsorbed to the liquid/liquid interface between the hydrophobic monomer and the hydrophilic solvent.

As described above, the O/W emulsion structure can be confirmed, for example, by observation with an optical microscope. The average particle size of the O/W emulsion is preferably 1 μm or more and 1000 μm or less. Moreover, in the O/W emulsion structure, the thickness of the coating layer 2 (micronized cellulose layer) formed on the surface layer of the droplets 5B is not particularly limited, but is preferably 3 nm or more and 1000 nm or less.

The weight ratio of the dispersion of the micronized cellulose 1 and the polymer mixture that can be used in step b3 is not particularly limited; however, the amount of the polymer mixture is preferably 1 part by mass or more and 50 parts by mass or less based on 100 parts by mass of the micronized cellulose 1. It is not preferable that the amount of the polymer mixture is less than 1 part by mass, because the yield of the composite particles 4 tends to decrease. It is also not preferable that the amount of the polymer mixture exceeds 50 parts by mass, because it tends to be difficult to uniformly coat the droplets 5B with the micronized cellulose 1.

(Step b4)

Step b4 is a step of removing the organic solvent from the polymer droplets 5B obtained in step b3 to solidify the polymer to form core particles 3 containing the polymer and the functional component, thereby obtaining sustained-release composite particles having the micronized cellulose 1 coating at least a part of the surface of the core particles 3, wherein the core particles 3 and the micronized cellulose 1 are inseparable from each other.

Specifically, the solvent is evaporated and removed by heating or/and drying under reduced pressure. When the boiling point of the organic solvent to be removed is lower than that of water, the organic solvent can be selectively removed. Although it is not particularly limited, the solvent can be efficiently removed by heating under reduced pressure conditions. The heating temperature is preferably 20° C. or higher and 100° C. or lower, and the pressure is preferably 600 mmHg or higher and 750 mmHg or lower.

Through the steps described above, it is possible to produce spherical composite particles 4 in which core particles 3 are coated with micronized cellulose 1. Immediately after the formation of the composite particles 4, a large amount of water and free micronized cellulose 1 that does not contribute to the formation of the coating layer 2 of the composite particles 4 remain mixed in the dispersion of the composite particles 4. Therefore, the composite particles 4 may be collected and purified by the same method as in the production method a, and the residual solvent may be removed in the same manner as in the production method a.

(Effects of Composite Particles 4)

The sustained-release composite particles 4 according to the present embodiment protect functional components from ultraviolet rays, heat, oxygen, etc., due to the characteristics of the micronized cellulose 1 (cellulose nanofibers), such as gas barrier properties, hydrophilicity, heat resistance, and high strength; have improved or even excellent dispersion stability and thus improved or even excellent sustained-release properties; and exhibit long-term effects. Further, the sustained-release composite particles 4 according to the present embodiment are economical because the frequency of use of functional components can be reduced due to their improved or even excellent sustained-release properties, and the environmental load can be reduced.

In addition, it is possible to provide a method for producing sustained-release composite particles 4 that efficiently encapsulate raw materials of functional components in a simple manner, and that reduce pollution due to disposal thereof.

Furthermore, the use of a biodegradable polymer as the polymer contained in the core particles 3 makes it possible to provide sustained-release composite particles that are decomposed when used as pesticides or drugs, that are safe, and that can suppress environmental pollution.

It is possible to provide sustained-release composite particles 4 in a new handling mode while maintaining the characteristics of micronized cellulose 1.

It is presumed that since the micronized cellulose 1 coats the surface of the core particles 3 in a state in which the micronized cellulose 1 and the core particles 3 are inseparable from each other, the functional component encapsulated in the core particles 3 is released more slowly than that in the case of the core particles 3 alone, thereby improving the sustained-release properties.

The surface of sustained-release particles encapsulating a functional component in a gel-like substance is in a wet state, and the particle surface is dried when soil or dust is attached to the surface; thus, the use environment has been limited. On the other hand, since the surface of the sustained-release composite particles 4 according to the present embodiment is in a dry state, they can be used even in a place where it is difficult to apply sustained-release particles using a gel-like substance.

In addition, it is possible to provide a method for producing sustained-release composite particles 4 that efficiently encapsulate raw materials of functional components in a simple manner without adding additives, such as surfactants, and that reduce pollution due to disposal thereof.

Further, since the micronized cellulose 1 is fibrous cellulose composed of cellulose, which is a biodegradable polymer, the use of a biodegradable polymer as the polymer contained in the core particles 3 makes it possible to provide sustained-release composite particles 4 that are decomposed when used as pesticides or drugs, that are safe, and that can suppress environmental pollution.

An embodiment according to the present invention was explained in detail above with reference to the drawings. However, specific configurations are not limited to this embodiment, and design changes and the like within a range not deviating from the spirit of the present invention are also included. Further, the components described in the embodiments can be combined with each other as appropriate.

For example, the core particles 3 may contain other components in addition to the polymer and the functional component. In addition, the coating layer 2 may contain components, other than the micronized cellulose 1, to adjust the sustained-release properties, or may contain functional materials.

(Addition of Functionality to Coating Layer 2)

In the composite particles 4 according to the present embodiment, a functional material other than cellulose may be added to the micronized cellulose 1 of the coating layer 2 on the surface thereof. In the above embodiment, examples of functional materials, other than cellulose, added to the surface of the composite particles 4 include magnetic substances, drugs, pesticides, perfumes, adhesives, enzymes, pigments, dyes, deodorants, metals, metal oxides, inorganic oxides, and like functional materials.

The composite particles 4 with functionality imparted to the coating layer 2 can be produced by using functionality-imparted micronized cellulose in which a functional material is previously added to the micronized cellulose 1. Further, the functional material may be added to the coating layer 2 after the composite particles 4 are produced.

The composite particles 4 with functionality imparted to the coating layer 2 can be produced, for example, by the following method. Specifically, the method comprises a step of fibrillating a cellulose raw material in a solvent to obtain a dispersion of micronized cellulose 1; a step of incorporating at least one type of polymerizable monomer and at least one type of functional component; a step of coating, with the micronized cellulose 1, at least a part of the surface of polymerizable monomer droplets 5A containing the polymerizable monomer and the functional component in the dispersion of the micronized cellulose 1 to stabilize the polymerizable monomer droplets 5A as an emulsion; and a step of polymerizing the polymerizable monomer droplets 5A in a state in which at least a part of the surface of the polymerizable monomer droplets 5A is coated with the micronized cellulose 1, to form core particles 3 containing the polymer and the functional component, thereby obtaining composite particles 4 in which at least a part of the surface of the core particles 3 is coated with the micronized cellulose 1; and further comprising a step of adding a functional material other than cellulose to at least a part of the micronized cellulose 1 on the surface of the composite particles 4.

Further, the composite particles 4 with functionality imparted to the coating layer 2 can also be produced by the following method. Specifically, the method comprises a step of fibrillating a cellulose raw material in a solvent to obtain a dispersion of micronized cellulose 1; a step of producing a micronized cellulose composite that is a composite of a functional material other than cellulose with the micronized cellulose 1 in the dispersion of the micronized cellulose 1; a step of preparing a polymerizable monomer mixture containing at least one type of polymerizable monomer and at least one type of functional component; a step of coating, with the micronized cellulose composite, at least a part of the surface of droplets 5A containing the polymerizable monomer in the dispersion of the micronized cellulose composite to stabilize the droplets 5A as an emulsion; and a step of polymerizing the polymerizable monomer in a state in which at least a part of the surface of the droplets 5A is coated with the micronized cellulose 1 to form core particles 3 containing the functional component and the polymer, thereby obtaining composite particles 4 in which at least a part of the surface of the core particles 3 is coated with the micronized cellulose composite.

The functional material is particularly preferably fine particles containing a metal. It is known that metals absorb and scatter light of a specific wavelength by localized surface plasmon resonance (hereinafter also referred to as LSPR) when the average particle size is reduced to submicron order (1 μm or less), for example.

The shape of the metal fine particles is not particularly limited, but may be, for example, a flat plate shape or a rod shape. In particular, when the metal fine particles contain gold or silver or both of them, the localized surface plasmon resonance wavelength can be widely controlled in the visible to near infrared region by forming the metal fine particles in a flat plate shape.

In general, when the solvent is completely removed from metal fine particles, the metal particles form strong aggregates or fuse together, which makes it difficult to redisperse nanoparticles at the primary particle level. Thus, there was a problem that the localized surface plasmon resonance effect cannot be used after redispersion. However, in the composite particles 4, metal fine particles are carried and fixed on the surface of the composite particles, and the composite particles 4 themselves have a high dispersibility due to the micronized cellulose 1 on the surface of the composite particles 4; thus, they can be easily redispersed, and can be treated as a dry powder that can use the localized surface plasmon effect.

The composition of the metal fine particles preferably contains, for example, at least one metal selected from gold, silver, platinum, and palladium, or a compound thereof, but is not particularly limited thereto. When a plurality of metal species are used, for example, precipitated fine silver particles may be coated with a metal nobler than silver or a metal oxide such as silica to improve the stability of the silver fine particles.

In the present embodiment, particles in a "flat plate shape" refer to plate-like particles having a substantially flat plate shape, and having an average aspect ratio (average particle size/average particle thickness) of 2.0 or more, determined by dividing the average particle size across the major surface by the average particle thickness.

The shape of the major surface is not particularly limited. For example, the particle size (circle-equivalent particle size) of a circle having the same area as that of the main plane is calculated. The average particle size and the average thickness are obtained, for example, by measuring 100 particles with an electron microscope, and calculating the average value thereof.

The average particle size of the flat plate-like metal fine particles is preferably 20 nm or more and 1000 nm or less. The average particle thickness of the flat plate-like metal fine particles is preferably 5 nm or more and 100 nm or less, and more preferably 8 nm or more and 50 nm or less. The average aspect ratio (average particle size/average particle thickness) is preferably 2.0 or more, and more preferably 2.0 or more and 200 or less.

First Examples

Hereinafter, the present invention will be described in detail based on first examples. However, the technical scope of the present invention is not limited to these examples. In the following examples, % indicates % by mass (w/w %) unless otherwise noted.

Example 1-1

(Step a1: Step of Obtaining Micronized Cellulose Dispersion)
(TEMPO Oxidation of Wood Cellulose)

70 g of softwood kraft pulp was suspended in 3500 g of distilled water, and a solution obtained by dissolving 0.7 g of TEMPO and 7 g of sodium bromide in 350 g of distilled water was added, followed by cooling to 20° C. 450 g of sodium hypochlorite aqueous solution with 2 mol/L and a density of 1.15 g/mL was added dropwise, whereby the oxidation reaction was started. The temperature in the system was kept constant at 40° C. The pH was prevented from lowering and maintained at pH 10 by adding a 0.5 N sodium hydroxide aqueous solution. When the total amount of sodium hydroxide added reached 3.50 mmol/g based on the weight of cellulose, approximately 100 mL of ethanol was added to stop the reaction. Thereafter, filtering and washing were repeated with distilled water by means of a glass filter, whereby oxidized pulp (oxidized cellulose) was obtained.
(Measurement of the Amount of Carboxyl Groups in Oxidized Cellulose)

The oxidized pulp and reoxidized pulp obtained by TEMPO oxidation were weighed at a solid content weight of 0.1 g and dispersed in water at a concentration of 1%, and hydrochloric acid was added to adjust the pH to 2.5. Thereafter, the amount of carboxyl groups (mmol/g) was determined by conductometric titration using a 0.5 M sodium hydroxide aqueous solution. The result was 1.6 mmol/g.
(Fibrillation Treatment of Oxidized Cellulose)

1 g of the oxidized cellulose obtained by TEMPO oxidation was dispersed in 99 g of distilled water, and micronized by a juicer mixer for 30 minutes to obtain a micronized cellulose water dispersion with a concentration of 1%.
(Evaluation of Micronized Cellulose 1)

Figure 4:
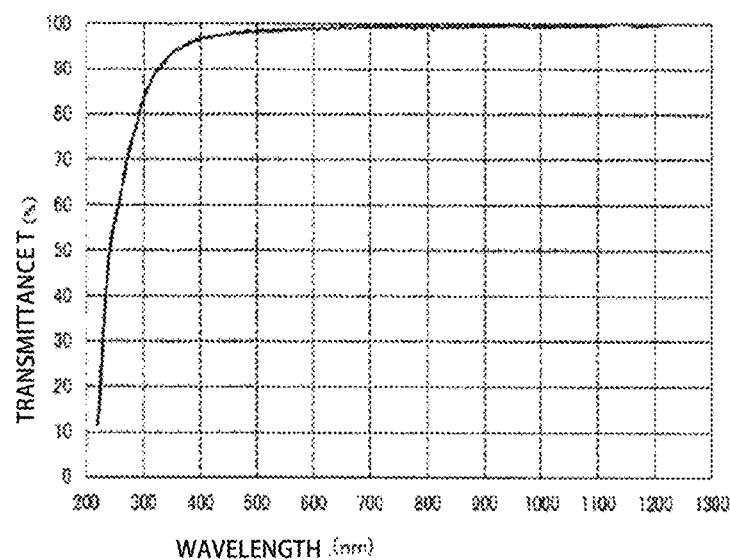
FIG. 4 shows the results of measuring the spectral transmission spectrum of a water dispersion of micronized cellulose obtained in Example 1-1 (2-1).
Figure 5:
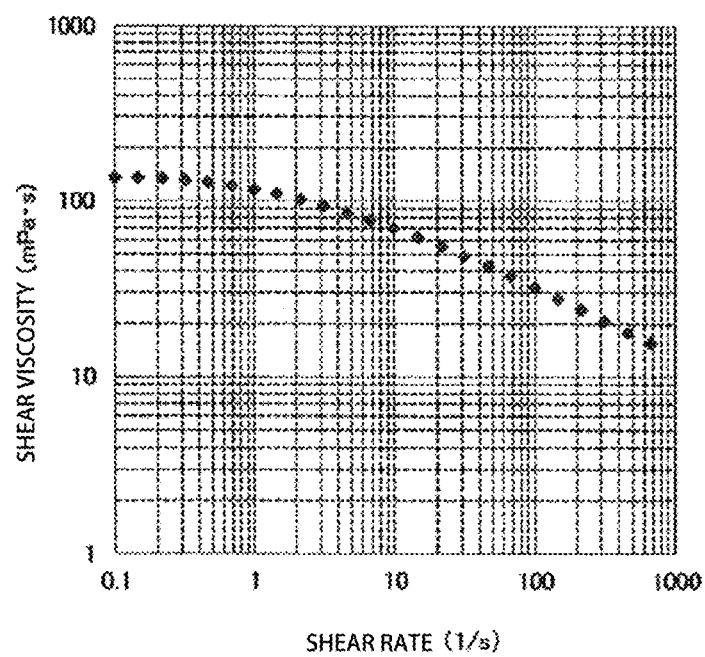
FIG. 5 shows the results of measuring the static viscoelasticity of the water dispersion of micronized cellulose obtained in Example 1-1 (2-1), using a rheometer.

The obtained oxidized cellulose and micronized cellulose 1 were measured and calculated for the amount of carboxyl groups, the degree of crystallinity, the number average major axis diameter, the light transmittance, and the rheology in the following manner. Table 1, FIG. 4, and FIG. 5 show the evaluation results of the obtained micronized cellulose 1.
(Measurement of the Amount of Carboxyl Groups)

The oxidized cellulose before dispersion treatment was measured to determine the amount of carboxyl groups in the following manner.

0.2 g of oxidized cellulose on a dry weight basis was placed in a beaker, and 80 ml of ion-exchanged water was added.

5 mL of 0.01 mol/L sodium chloride aqueous solution was added thereto, and 0.1 mol/L hydrochloric acid was added while stirring to adjust the pH to 2.8 as a whole.

Then, a 0.1 mol/L sodium hydroxide aqueous solution was poured thereinto at 0.05 mL/30 sec using an automatic titrator (trade name: AUT-701, produced by DKK-TOA Corporation), and the conductivity and pH value were measured every 30 seconds. The measurement was continued to a pH of 11.

The titer of sodium hydroxide was determined from the obtained conductivity curve, and the content of carboxyl groups was calculated.

(Calculation of the Degree of Crystallinity)

The degree of crystallinity of the TEMPO-oxidized cellulose was calculated.

The X-ray diffraction pattern of the TEMPO-oxidized cellulose was measured using a versatile X-ray diffraction system equipped with a high precision horizontal sample stage (trade name: Ultima III, produced by Rigaku Corporation) in the range of 5°≤2θ≤35° under the conditions of X-ray output: (40 kv, 40 mA). Because the X diffraction pattern obtained was derived from the cellulose I type crystal structure, the degree of crystallinity of the TEMPO-oxidized cellulose was calculated by the method shown below using the following formula (1):

$$\text{Degree of crystallinity (\%)} = [(I22.6 - I18.5)/I22.6] \times 100 \quad (1)$$

In the formula, I22.6 represents the diffraction intensity of a lattice plane (002 plane) (diffraction angle 2θ=22.6°) in the X-ray diffraction, and I18.5 represents the diffraction intensity of an amorphous part (diffraction angle 2θ=18.5°).

(Calculation of Number Average Major Axis Diameter of Micronized Cellulose 1)

The number average major axis diameter of the micronized cellulose 1 was calculated using an atomic force microscope.

First, a micronized cellulose water dispersion was diluted to 0.001%, and every 20 μL thereof was then cast on a mica plate, followed by air-drying.

After drying, the shape of the micronized cellulose 1 was observed using an atomic force microscope (trade name: AFM5400L, produced by Hitachi High-Technologies Corp.) in the DFM mode.

The number average major axis diameter of the micronized cellulose 1 was determined as the average value of the major axis diameters (maximum diameters) of 100 fibers measured from an image observed by the atomic force microscope.

(Measurement of Light Transmittance of Water Dispersion of Micronized Cellulose 1)

The light transmittance of the micronized cellulose water dispersion was measured.

Water was used as a reference in one of sample cells made of quartz, and the micronized cellulose water dispersion was put in the other sample cell so that air bubbles were not formed. The light transmittance at wavelengths of 220 nm to 1300 nm with an optical path length of 1 cm was measured by a spectrophotometer (trade name: NRS-1000, produced by JASCO Corporation). FIG. 4 shows the results.

(Rheology Measurement)

The rheology of a dispersion of 0.5 mass % micronized cellulose was measured by a rheometer (trade name: AR2000ex, produced by TA Instruments) on a cone plate with a tilt angle of 1°.

The temperature of the measurement site was adjusted to 25° C., and the shear viscosity was measured continuously at a shear rate of 0.01 s$^{-1}$ to 1000 s$^{-1}$. FIG. 5 shows the results. As is clear from FIG. 5, the micronized cellulose dispersion was thixotropic. Table 1 shows shear viscosity at a shear rate of 1 s$^{-1}$ and 100 s$^{-1}$.

TABLE 1

| Amount of carboxyl groups (mmol/g) | Degree of crystallinity (%) | Number average minor axis diameter (nm) | Number average major axis diameter (nm) | Transmittance (%) | Shear viscosity (mPa · s) | |
|---|---|---|---|---|---|---|
| | | | | | [1 s − 1] | [100 s$^{-1}$] |
| 1.37 | 81 | 3 | 418 | 99.2 | 116.5 | 32.2 |

As is clear from FIG. 4, the micronized cellulose water dispersion showed a high transparency. Moreover, the micronized cellulose 1 (TEMPO-oxidized CNF) contained in the micronized cellulose water dispersion had a number average minor axis diameter of 3 nm and a number average major axis diameter of 418 nm. Further, FIG. 5 shows the results of static viscoelasticity measurement using a rheometer. As is clear from FIG. 5, the micronized cellulose water dispersion was thixotropic.

(Step a2: Step of Preparing Polymerizable Monomer Mixture)

Next, 1 g of 2,2-azobis-2,4-dimethylvaleronitrile (hereinafter also referred to as ADVN) as a polymerization initiator was dissolved in 10 g of divinylbenzene (hereinafter also referred to as DVB) as a polymerizable monomer. Further, 2 g of pesticide fenitrothion (Sumithion, MEP, produced by Sumitomo Chemical Co., Ltd.) as a functional component was added and mixed.

(Step a3: Step of Producing O/W Emulsion)

When the total amount of the polymerizable monomer mixture prepared in step a2 was added to 40 g of micronized cellulose dispersion with a micronized cellulose concentration of 1%, the polymerizable monomer mixture and the micronized cellulose dispersion were separated into two phases each in a highly transparent state.

Next, the shaft of an ultrasonic homogenizer was inserted via the liquid surface of the upper phase in the mixture in the two-phase separated state, and ultrasonic homogenizer treatment was performed for 3 minutes at a frequency of 24 kHz and an output of 400 W. The appearance of the mixture after ultrasonic homogenizer treatment resembled a cloudy emulsion. When a drop of the mixture was added to a glass slide, sealed with cover glass, and observed with a light microscope, it was confirmed that an enormous number of emulsion droplets in size of about 1 to several μm were formed, and that they were dispersed and stabilized as an O/W emulsion.

(Step a4: Step of Obtaining Composite Particles 4)

The O/W emulsion dispersion was placed in a hot-water bath at 70° C., and treated by stirring with a stirrer for 8 hours to carry out the polymerization reaction. The dispersion was cooled to room temperature after the 8-hour treatment. The appearance of the dispersion did not change before and after the polymerization reaction. When the obtained dispersion was treated at a centrifugal force of 75,000 g (g: gravitational acceleration) for 5 minutes, a precipitate was obtained. The supernatant was removed by decantation, and the precipitate was collected. Further, the precipitate was repeatedly washed with purified water and methanol using a PTFE membrane filter with a pore size of 0.1 μm. The thus-obtained purified and collected product was redispersed at a concentration of 1%, and the particle size was evaluated using a particle size distribution meter (Nanotrac UPA-EX150, produced by Nikkiso Co., Ltd.). As a result, the average particle size was found to be 2.1 μm. Next, the purified and collected product was air-dried, and further vacuum-dried at room temperature (25° C.) for 24 hours. As a result, a fine dry powder (composite particles 4) was obtained.

(Shape Observation with Scanning Electron Microscope)

Figure 6:
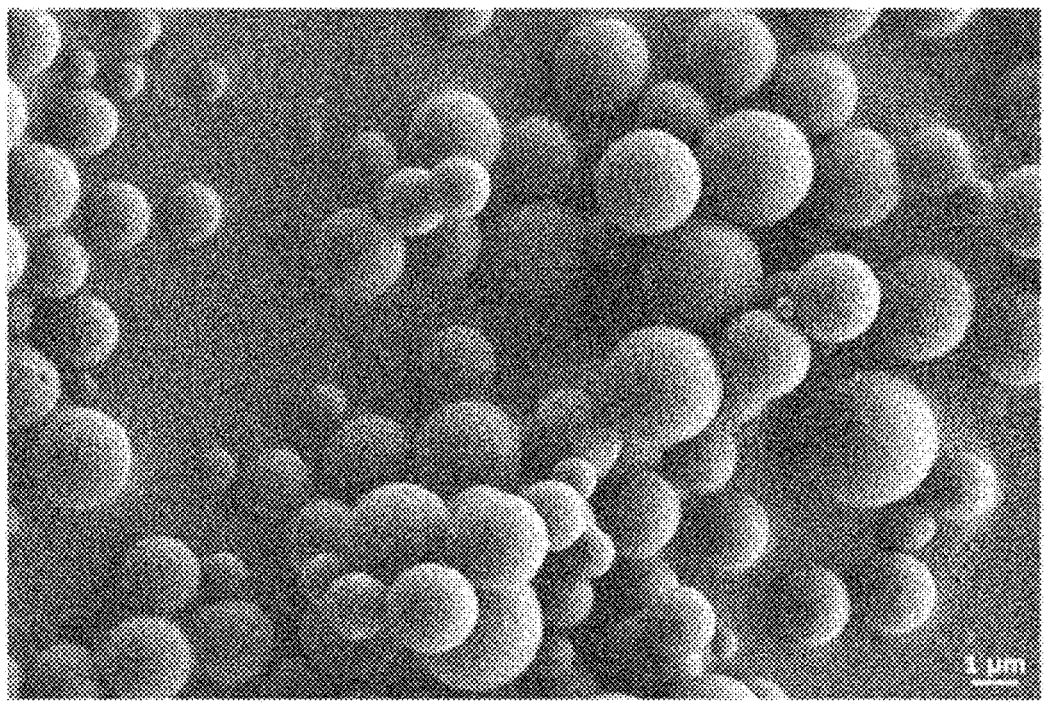
FIG. 6 shows a figure (an SEM image) showing the results of observing composite particles obtained in Example 1-1 (2-1) with a scanning electron microscope (SEM).
Figure 7A:
FIGS. 7(a) and 7(b) show figures (SEM images) showing the results of observing the composite particles obtained in Example 1-1 (2-1) with a scanning electron microscope (SEM) at high magnification.
Figure 7B:
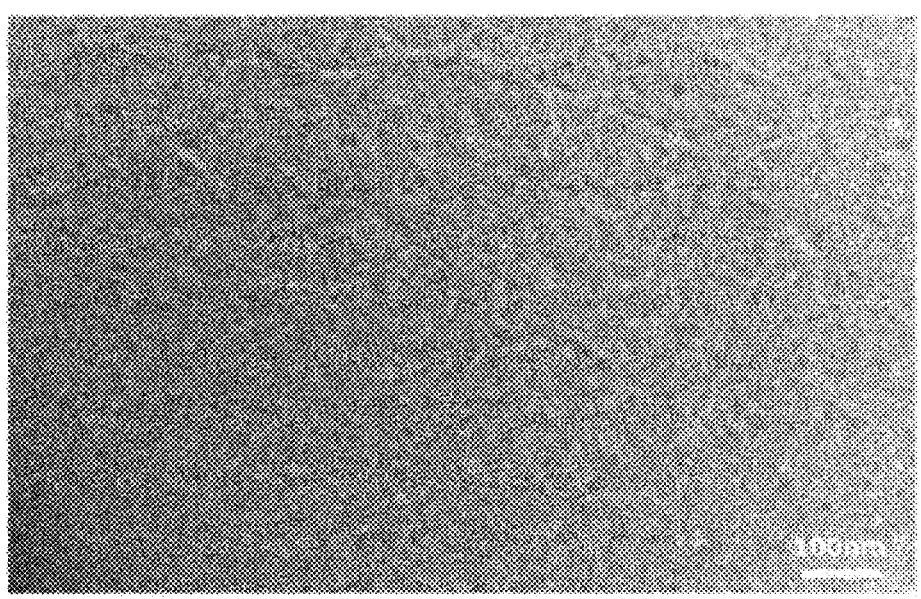

FIGS. 6 and 7 show the results of observing the obtained dry powder with a scanning electron microscope. As is clear from FIG. 6, it was confirmed that the polymerization reaction performed using O/W emulsion droplets as a template resulted in the formation of an enormous number of spherical composite particles 4 derived from the shape of the emulsion droplets. Further, as shown in FIGS. 7 (a) and (b), it was confirmed that their surface was uniformly coated with several-nanometer-wide micronized cellulose 1. Moreover, the surface of the composite particles 4 was equally and uniformly coated with the micronized cellulose 1, even after washing was repeated by filtration washing. Therefore, it was indicated that in the composite particles 4 of the present embodiment, the monomer in the composite particles 4 and the micronized cellulose 1 were bonded and inseparable from each other.

(Evaluation of Redispersibility)

When the dry powder of the composite particles 4 was added to purified water at a concentration of 1% and redispersed by a stirrer, the dry powder was easily redispersed, and no aggregation was observed. Moreover, when the particle size was evaluated using a particle size distribution meter, the average particle size was 2.1 μm as with that before drying, and the data from the particle size distribution meter did not show any signal indicating aggregation.

The above results indicated that although the surface of the composite particles 4 was coated with the micronized cellulose 1, they were obtained as a powder by drying without forming a film, and had improved or even excellent redispersibility.

Example 1-2

Composite particles 4 according to Example 1-2 were produced in the same manner as in Example 1-1, except that diethylene glycol diacrylate (trade name: FA-222A, Hitachi Chemical Co., Ltd.; hereinafter also referred to as FA-222A) was used in place of DVB in Example 1-1.

Example 1-3

Composite particles 4 according to Example 1-3 were produced in the same manner as in Example 1-1, except that hexanediol diacrylate (trade name: A-HD-N, Shin Nakamura Chemical Co., Ltd.; hereinafter also referred to as A-HD-N) was used in place of DVB in Example 1-1.

Example 1-4

Composite particles 4 according to Example 1-4 were produced in the same manner as in Example 1-1, except for using a carboxymethylated CNF dispersion obtained by performing carboxymethylation (hereinafter also referred to as carboxymethylated CNF) according to PTL 4 cited as the prior art, in place of TEMPO oxidation in Example 1-1.

Example 1-5

Composite particles 4 according to Example 1-5 were produced in the same manner as in Example 1-1, except for using a phosphorylated CNF dispersion obtained by performing phosphorylation according to NPL 1 cited as the prior art, in place of TEMPO oxidation in Example 1-1.

Example 1-6

(Step b1: Step of Obtaining Micronized Cellulose Dispersion)

A micronized cellulose dispersion was obtained under the same conditions as in Example 1-1.

(Step b2: Step of Preparing Polymer Solution)

Next, 10 g of polylactic acid (PLA) was dissolved in 100 g of dichloroethane, and 2 g of fenitrothion (Sumithion, MEP) was added and mixed to prepare a polymer solution.

(Step b3: Step of Producing O/W Emulsion)

When the total amount of the polymer solution obtained in step b2 was added to 500 g of micronized cellulose dispersion with a micronized cellulose 1 concentration of 1%, the polymer solution and the micronized cellulose dispersion were separated into two phases each in a highly transparent state.

Next, from the liquid surface of the upper phase in the mixture in the two-phase separated state, ultrasonic homogenizer treatment was carried out using an ultrasonic homogenizer in the same manner as in step a3 of Example 1-1. It was confirmed with an optical microscope that an enormous number of emulsion droplets in size of about 1 to several μm were formed, and that they were dispersed and stabilized as an O/W emulsion.

(Step b4: Step of Obtaining Composite Particles 4)

The O/W emulsion liquid obtained in step b3 was vacuum-dried under reduced pressure of 700 mmHg at 40° C. for 3 hours to completely evaporate the dichloroethane. The appearance of the dispersion did not change between before and after the evaporation of the dichloroethane.

The obtained dispersion was separated and purified under the same conditions as in Example 1-1. The average particle size of the obtained composite particles 4 was 2.8 μm. When the collected product was dried under the same conditions as in Example 1-1, a fine dry powder (composite particles 4) was obtained.

Example 1-7

Micronized cellulose 1 was prepared under the same conditions as in step b1 in Example 1-6, 10 g of poly-ε-caprolactone (PCL, produced by Wako Pure Chemical Corporation) was dissolved in 200 g of ethyl acetate in step b2, and 2 g of fenitrothion (Sumithion, MEP, produced by Sumitomo Chemical Co., Ltd.) was added and mixed to prepare a polymer solution. Next, after an O/W emulsion liquid was prepared under the same conditions as in step b3, the O/W emulsion liquid was vacuum-dried under reduced pressure of 700 mgHg at 40° C. for 5 hours to completely evaporate the ethyl acetate in step b4. Except for the above, composite particles 4 according to Example 1-7 were obtained under the same conditions as in Example 1-6.

Example 1-8

Composite particles 4 according to Example 1-8 were produced under the same conditions as in Example 1-1, except that a fertilizer (isobutyraldehyde condensation urea: IB) was used in Example 1-1.

Example 1-9

Composite particles 4 according to Example 1-9 were produced under the same conditions as in Example 1-1, except that a fertilizer (isobutyraldehyde condensation urea: IB) was used in Example 1-6.

Example 1-10

Composite particles 4 according to Example 1-10 were produced under the same conditions as in Example 1-1, except that an antifungal agent 5,6-dichloro-2-n-octyl-4-isothiazoline-3-one (DCOIT) was used as the functional component in Example 1-1.

Example 1-11

Composite particles 4 according to Example 1-11 were produced under the same conditions as in Example 1-1, except that DCOIT was used in Example 1-6.

Comparative Example 1-1

Composite particles according to Comparative Example 1-1 were produced under the same conditions as in Example 1-1, except that purified water was used in place of the TEMPO-oxidized CNF dispersion in Example 1-1.

Comparative Example 1-2

Composite particles according to Comparative Example 1-2 were produced under the same conditions as in Example 1-1, except that a carboxymethyl cellulose (hereinafter also referred to as CMC) aqueous solution was used in place of the TEMPO-oxidized CNF dispersion in Example 1-1.

Comparative Example 1-3

An attempt was made to produce composite particles according to Comparative Example 1-3 under the same conditions as in Example 1-8, except that a carboxymethyl cellulose (hereinafter also referred to as CMC) aqueous solution was used in place of the TEMPO-oxidized CNF dispersion in Example 1-8.

Comparative Example 1-4

An O/W emulsion liquid was prepared using an aqueous solution obtained by dissolving 8 parts by mass of polyvinyl alcohol (PVA) and 0.5 parts by mass of polyglyceryl laurate-10 (PGLE ML10) in 500 g of purified water, in place of the micronized cellulose dispersion in step b1 of Example 1-6. Steps b2 and b3 were performed under the same conditions as in Example 1-6. The obtained O/W emulsion liquid was spray-dried at a drying temperature of 100° C. using a spray dryer to produce particles according to Comparative Example 1-4.

Comparative Example 1-5

Particles according to Comparative Example 1-5 were produced under the same conditions as in Comparative Example 1-4, except that IB was used in place of MEP as the functional component in Comparative Example 1-4.

Comparative Example 1-6

Particles according to Comparative Example 1-6 were produced under the same conditions as in Comparative Example 1-4, except that DCOIT was used in place of MEP as the functional component in Comparative Example 1-4.

Comparative Example 1-7

An attempt was made to produce particles according to Comparative Example 1-7 under the same conditions as in Comparative Example 1-4, except that polyglyceryl laurate-10 (PGLE ML10) was not added in Comparative Example 1-4.

<Evaluation Method>
(Evaluation of Whether Composite Particles were Formed)

Whether composite particles were formed was determined by shape observation with a scanning electron microscope. The obtained dry powder was observed with a scanning electron microscope. Whether composite particles 4 were formed was determined on the following criteria.

++: Spherical particles were obtained, and their surface was coated with micronized cellulose.
+: Spherical particles were obtained, but their surface was not coated with micronized cellulose.
−: Such particles were not obtained.

(Evaluation of Dispersion Stability)

The dry powder of the composite particles 4 was added to purified water at a concentration of 1%, and redispersed with a stirrer. After the resultant was allowed to stand at 25° C. for 2 weeks, examination was performed to check for aggregation. The dispersion stability was determined on the following criteria.

++: No aggregates were visually confirmed.
−: Aggregates were visually confirmed.

(Evaluation of Sustained-Release Properties)

The sustained-release properties were evaluated by the test of elution of the functional component in water. 0.1 g of composite particles 4 were added to 500 mL of distilled water, followed by shaking at 250 rpm at 25° C. Then, the test liquid was filtered, and the concentration of the eluted functional component was measured using a high-performance liquid chromatographic measurement device (produced by Shimadzu Corporation). The total amount of functional component gradually released in the aqueous solution from the start of sustained release to the completion of the test (the amount of sustained release) was determined, and the elution ratio was defined as the amount of sustained release relative to the amount of functional component encapsulated in the composite particles 4 during preparation (initial content) (elution ratio=the amount of sustained release/initial content×100). The initial content was measured by grinding the composite particles 4 with a mortar, and then dissolving the functional component in a solvent. The sustained-release properties were determined on the following criteria.

++: The elution ratio was less than 50% within 100 hours after the start of sustained release.
−: The elution ratio was 50% or more within 100 hours after the start of sustained release.

(Evaluation of Insecticidal Effect)

The insecticidal effect against scarab beetle larvae was evaluated. The composite particles 4 were mixed with soil at 0.1 g/m², and 10 scarab beetles were introduced after 40 days. Then, the mortality after 7 days was examined. The insecticidal effect was determined on the following criteria.

++: The mortality was 90% or more.
−: The mortality was less than 90%.

(Evaluation of Fertilizer Effect)

The fertilizer effect of the composite particles 4 for grass was evaluated. *Zoysia matrella* Merr. was fertilized with the composite particles 4 at 25 g/m². The growth of the overground part of the plant 40 days after fertilization was observed. The fertilizer effect was determined on the following criteria.

++: The grass blade was hard, and the leaf color was good.
−: The grass blade was not hard, or the leaf color was not good.

(UV Resistance Test)

In the ultraviolet (UV) resistance test, the obtained particles were added to a PVA solution to 0.1 parts by mass, and after stirring with a stirrer for 1 hour, the mixture was applied to an aluminum plate using an applicator to a film thickness of 10 μm, followed by air drying overnight to produce a coating film. The coating film was irradiated with UV at 30 μW/cm² with a black light, and the DCOIT residual ratio after 2 weeks was measured.

The residual ratio was determined by the residual amount relative to the initial content (residual ratio=residual amount/initial content×100). The UV resistance was determined on the following criteria.

++: The residual ratio after 2 weeks was 20% or more.
−: The residual ratio after 2 weeks was less than 20%.

(Evaluation of Biodegradability)

The biodegradability was evaluated based on the JIS standard "JIS K6950: 2000 Determination of the ultimate aerobic biodegradability of plastic materials in an aqueous medium—Method by measuring the oxygen demand in a closed respirometer." The composite particles 4 and activated sludge were added to an inorganic salt medium to 100 mg/L and 30 mg/L, respectively. The amount of oxygen consumption was measured, and the oxygen consumption biochemical oxygen demand (BOD; mass concentration of dissolved oxygen when a chemical substance or an organic substance is consumed by aerobic biological oxidation in water under specified conditions) was calculated.

An inorganic salt medium free from the composite particles 4 was used as a control. The amount of oxygen required for all the composite particles 4, except for the functional component, to be converted to water and carbon dioxide gas (theoretical oxygen demand, ThOD) was calculated from the polymer composition formula. The degree of biodegradation was calculated as biochemical oxygen demand relative to theoretical oxygen demand (degree of biodegradation=BOD/ThOD×100). The biodegradability was determined on the following criteria.

++: The degree of biodegradation 28 days after the start of the test was 80% or more.
−: The degree of biodegradation 28 days after the start of the test was less than 80%.

The following Tables 2 to 4 collectively show the evaluation results using the above examples and comparative examples. Table 2 shows the examples and comparative examples using pesticide MEP as the functional component, Table 3 shows the examples and comparative examples using fertilizer IB as the functional component, and Table 4 shows the examples and comparative example using antifungal agent DCOIT as the functional component.

TABLE 2

| | Emulsion stabilizer | Polymer | Functional component | Composite particles | Dispersion stability | Sustained-release properties | Insecticidal properties |
|---|---|---|---|---|---|---|---|
| | | | | | | MEP | |
| Example 1-1 | TEMPO-oxidized CNF | DVB polymer | MEP | ++ | ++ | ++ | ++ |
| Example 1-2 | TEMPO-oxidized CNF | FA-222A polymer | MEP | ++ | ++ | ++ | ++ |
| Example 1-3 | TEMPO-oxidized CNF | A-HD-N polymer | MEP | ++ | ++ | ++ | ++ |
| Example 1-4 | Carboxymethylated CNF | DVB polymer | MEP | ++ | ++ | ++ | ++ |
| Example 1-5 | Phosphorylated CNF | DVB polymer | MEP | ++ | ++ | ++ | ++ |
| Example 1-6 | TEMPO-oxidized CNF | PLA | MEP | ++ | − | + | ++ |
| Example 1-7 | TEMPO-oxidized CNF | PCL | MEP | ++ | − | + | ++ |
| Comparative Example 1-1 | None (only pure water) | DVB polymer | MEP | − | | | |
| Comparative Example 1-2 | CMC | DVB polymer | MEP | − | | | |
| Comparative Example 1-4 | PVA/PGLE ML10 | PLA | MEP | + | − | − | − |
| Comparative Example 1-7 | PVA | PLA | MEP | − | | | |

TABLE 3

| | Emulsion stabilizer | Polymer | Functional component | Composite particles | Dispersion stability | Sustained-release properties | Insecticidal properties |
|---|---|---|---|---|---|---|---|
| | | | | | | IB | |
| Example 1-8 | TEMPO-oxidized CNF | DVB polymer | IB | ++ | ++ | ++ | ++ |
| Example 1-9 | TEMPO-oxidized CNF | PLA | IB | ++ | ++ | ++ | ++ |
| Comparative Example 1-3 | CMC | DVB polymer | IB | − | | | |
| Comparative Example 1-5 | PVA/PGLE ML10 | PLA | IB | + | − | − | − |

TABLE 4

| | Emulsion stabilizer | Polymer | Functional component | Composite particles | Dispersion stability | DCOIT Sustained-release properties | Insecticidal properties |
|---|---|---|---|---|---|---|---|
| Example 1-10 | TEMPO-oxidized CNF | DVB polymer | DCOIT | ++ | ++ | ++ | ++ |
| Example 1-11 | TEMPO-oxidized CNF | PLA | DCOIT | ++ | ++ | ++ | ++ |
| Comparative Example 1-6 | PVA/PGLE ML10 | PLA | DCOIT | − | − | − | − |

The oblique lines in the cells of the comparative examples in Tables 2 and 3 indicate that the evaluation could not be conducted, and that the subsequent step was not carried out.

As is clear from the evaluation results of Examples 1-1 to 1-11 in Tables 2, 3, and 4, it was confirmed that regardless of the type of micronized cellulose 1 (TEMPO-oxidized CNF, carboxymethylated CNF, and phosphorylated CNF), composite particles 4 comprising polymers of various monomers or biodegradable polymers, and various function components as core particles 3 could be produced. Examples 1-6, 1-7, 1-9, and 1-11 successively had biodegradability even after micronized cellulose was formed on the polymers having biodegradability.

On the other hand, in Comparative Example 1-1, step a2 could not be performed. Specifically, the monomer phase and the micronized cellulose dispersion phase were kept in the two-phase separated state even after ultrasonic homogenizer treatment was carried out, and the production of an O/W emulsion itself was not possible.

In Comparative Example 1-7, step b2 could also not be performed. Specifically, the polymer phase and the micronized cellulose dispersion phase were kept in the two-phase separated state even after ultrasonic homogenizer treatment was carried out, and the production of an O/W emulsion itself was not possible.

In Comparative Examples 1-2 and 1-3, an O/W emulsion could be formed in step a2. This is considered to be because CMC had amphiphilicity as with the micronized cellulose 1, and functioned as a stabilizer for the emulsion. However, when the polymerization reaction was carried out in the subsequent step a3, the emulsion was destabilized, and composite particles using the O/W emulsion as a template could not be obtained. Although the reason for this is not clear, it is highly likely that CMC, which is water-soluble, is fragile as the coating layer 2 for maintaining the emulsion shape during the polymerization reaction, and it is thus considered that the emulsion was broken during the polymerization reaction.

In Comparative Examples 1-4 and 1-5, particles containing a polymer and a functional component could be produced; however, their surface was not coated with micronized cellulose 1.

As a result of evaluating the sustained-release properties of the functional component MEP encapsulated in the composite particles 4 of Examples 1-1 to 1-7, it was confirmed that the elution ratio was less than 50%, that the encapsulated functional component MEP was retained inside the composite particles 4 for a long period of time, and that there were improved or even excellent sustained-release properties. On the other hand, the particles of Comparative Example 1-4, the surface of which was not coated with micronized cellulose 1, did not have sufficient sustained-release properties. This suggested that the composite particles exhibited improved or even excellent sustained-release properties because their surface was coated with micronized cellulose 1.

Further, as a result of evaluating the sustained-release properties of the functional component IB encapsulated in the composite particles 4 of Examples 1-8 and 1-9, it was confirmed that the elution ratio was less than 50%, that the encapsulated functional component IB was retained inside the composite particles 4 for a long period of time, and that there were improved or even excellent sustained-release properties. On the other hand, the particles of Comparative Example 1-5, the surface of which was not coated with micronized cellulose 1, did not have sufficient sustained-release properties. This suggested that the composite particles 4 exhibited improved or even excellent sustained-release properties because their surface was coated with micronized cellulose 1.

Moreover, as a result of evaluating the sustained-release properties of the functional component DCOIT encapsulated in the composite particles 4 of Examples 1-10 and 1-11, it was confirmed that the elution ratio was less than 50%, that the encapsulated functional component DCOIT was retained inside the composite particles 4 for a long period of time, and that there were improved or even excellent sustained-release properties. On the other hand, the particles of Comparative Example 1-6, the surface of which was not coated with micronized cellulose 1, did not have sufficient sustained-release properties. This suggested that the composite particles 4 exhibited improved or even excellent sustained-release properties because their surface was coated with micronized cellulose 1.

As a result of evaluating the insecticidal properties of the composite particles 4 of Examples 1-1 to 1-7, in which MEP was encapsulated as the functional component, they exhibited improved or even excellent insecticidal properties even after 40 days from the start of the test. On the other hand, as a result of evaluating the insecticidal properties of the sample of Comparative Example 1-4, the insecticidal properties after 40 days from the start of the test were not sufficient. From this, it is considered that the encapsulated functional component was protected due to the coating effect of the micronized cellulose 1, and that because of sustained release, improved or even excellent insecticidal properties were exhibited even after 40 days.

As a result of evaluating the plant growth in Example 1-8, in which IB was encapsulated as the functional component, a high fertilizer effect was exhibited even 40 days after fertilization, and the plant growth state was good. On the other hand, in Comparative Example 1-5, the fertilizer effect after 40 days was not sufficient. From this, it is considered that the encapsulated functional component was protected due to the coating effect of the micronized cellulose 1, and that because of sustained release, an improved or even excellent fertilizer effect was exhibited even after 40 days.

As a result of evaluating the residual ratio of the functional component DCOIT encapsulated in the composite particles 4 of Examples 1-10 and 1-11 after UV exposure, it was confirmed that the residual ratio was 20% or more, that the encapsulated functional component DCOIT was retained inside the composite particles 4 without being decomposed, and that there was improved or even excellent UV resistance. On the other hand, the particles of Comparative Example 1-6, the surfaces of which were not coated with micronized cellulose 1, did not have sufficient UV resistance. This suggested that the composite particles 4 exhibited improved or even excellent UV resistance because their surface was coated with micronized cellulose 1.

Second Embodiment

The sustained-release composite particles described in the first embodiment have improved or even excellent dispersion stability and thus improved or even excellent sustained-release properties, and exhibit long-term effects, as described above. Accordingly, the above sustained-release composite particles may be used for interior materials, furniture, etc., of buildings, for example. This point will be described in detail below.

Some interior materials, furniture, etc., of buildings are produced using adhesives and binders containing formaldehyde, and some products contain formaldehyde. Because formaldehyde is released from such products, the released formaldehyde remains in the room, causing problems of health hazards to humans and animals. Accordingly, development of removers for removing formaldehyde has proceeded.

Examples of such removers include those using formaldehyde reactants that can react with formaldehyde to convert it into another compound. Formaldehyde can be removed by treating target products with such removers. For example, hydrazide compounds (see PTL 8 etc.) are known as formaldehyde reactants.

Moreover, some cases use a means for microencapsulation using an active component having a desired effect to maintain the effect for a long period of time, without significantly increasing the amount thereof used, and encapsulating the active component into microcapsules made of a film-forming component. The active component encapsulated into the microcapsules is gradually released to the outside of the microcapsules with time (shows sustained-release properties), and the effect of the active component is sustainable over a long period of time. Such techniques of microcapsules have actively been examined particularly in the fields of drugs, pesticides, etc. Microcapsules encapsulating a formaldehyde reactant have been proposed, in which the formaldehyde reactant is encapsulated into the microcapsules for microencapsulation, whereby the formaldehyde removal effect can be maintained over a long period of time (see PTL 9).

However, conventional removers using formaldehyde reactants, such as the one disclosed in PTL 8, were insufficient in terms of long-term sustainability for maintaining the formaldehyde removal effect over a long period of time, consequently causing a problem of use of a large amount of formaldehyde reactant. In addition, microcapsules encapsulating a formaldehyde reactant, such as those disclosed in PTL 9, can maintain the sustained-release properties of the formaldehyde reactant under a liquid environment for a long period of time; however, it is considered to be difficult to maintain the sustained-release properties of the formaldehyde reactant encapsulated in the microcapsules in a dry state.

The present embodiment has been made in view of such circumstances. The following will describe novel composite particles that have a long-lasting formaldehyde removal effect and are easy to handle while maintaining the characteristics of cellulose nanofibers, a method for producing the composite particles, a dry powder comprising the composite particles, and wallpaper comprising the composite particles.

<Micronized Cellulose/Polymer Composite Particles>

First, the composite particles 4 comprising micronized cellulose 1 and core particles 3 according to the second embodiment of the present invention will be described. The composite particles 4 according to the present embodiment are obtained by using an O/W Pickering emulsion using micronized cellulose 1, and polymerizing a polymerizable monomer in the emulsion, as with the composite particles 4 according to the first embodiment.

The composite particles 4 comprise at least one type of core particles 3, and have a coating layer 2 composed of micronized cellulose 1 on the surface of the core particles 3, the core particles 3 and the micronized cellulose 1 being bonded and inseparable from each other. More specifically, the composite particles 4 comprise at least one type of core particles 3 containing a formaldehyde reactant, and micronized cellulose 1 coating at least a part of the surface of the core particles 3, the core particles 3 containing a formaldehyde reactant and micronized cellulose 1 which are inseparable from each other.

The composite particles 4 according to the present embodiment can be formed in the same manner as for the composite particles 4 according to the first embodiment. For example, as shown in FIG. 2, the micronized cellulose 1 is adsorbed to the interface of polymerizable monomer droplets 5A dispersed in a dispersion 6, thereby stabilizing the O/W Pickering emulsion; and the monomer in the emulsion is polymerized while maintaining a stabilized state, thereby forming composite particles 4 using the emulsion as a template.

The other configurations etc. are the same as those of the first embodiment. Accordingly, the explanation thereof is omitted herein.

<Method c for Producing Composite Particles 4>

Next, an example of the method for producing composite particles 4 of the present embodiment will be described. The method for producing composite particles 4 according to the present embodiment comprises: a step of fibrillating a cellulose raw material in a solvent to obtain a dispersion of micronized cellulose 1 (step c1); a step of coating, with the micronized cellulose 1, at least a part of the surface of polymerizable monomer droplets 5A containing a formaldehyde reactant and a polymerizable monomer in the dispersion of the micronized cellulose 1 obtained in step c1, thereby stabilizing the polymerizable monomer droplets 5A as an emulsion (step c2); and a step of polymerizing the polymerizable monomer droplets 5A in a state in which at least a part of the surface of the polymerizable monomer droplets 5A is coated with the micronized cellulose 1, to form core particles 3, thereby coating at least a part of the surface of the core particles 3 with the micronized cellulose 1, and making the core particles 3 and the micronized cellulose 1 inseparable from each other (step c3). Thus, the method c for producing composite particles 4 according to the present embodiment is almost the same as the method a for producing composite particles 4 according to the first embodiment described above.

Hereinafter, each of the steps will be described in detail.
(Step c1)

Step c1 according to the present embodiment is the same as step a1 according to the first embodiment described above. Accordingly, the explanation thereof is omitted herein.
(Step c2)

Step c2 is a step of coating, with the micronized cellulose 1, at least a part of the surface of polymerizable monomer droplets 5A mixed with a formaldehyde reactant in the dispersion of the micronized cellulose 1, thereby stabilizing the polymerizable monomer droplets 5A as an emulsion.

Specifically, in this step, a polymerizable monomer mixed with a formaldehyde reactant is added to the micronized cellulose dispersion obtained in step c1, the polymerizable monomer is dispersed as droplets in the micronized cellulose dispersion, and at least a part of the surface of the polymerizable monomer droplets 5A is coated with the micronized cellulose 1, thereby producing an O/W emulsion stabilized by the micronized cellulose 1.

The method for producing an O/W emulsion according to the present embodiment is substantially the same as the method for producing an O/W emulsion according to the first embodiment described above. Accordingly, the explanation thereof is omitted herein.

The O/W emulsion structure can be confirmed, for example, by observation with an optical microscope. The particle size of the O/W emulsion is not particularly limited, but is generally about 0.1 μm to 1000 μm.

In the O/W emulsion structure, the thickness of the micronized cellulose layer (coating layer) 2 formed on the surface layer of the polymerizable monomer droplets 5A is not particularly limited, but is generally about 3 nm to 1000 nm. The thickness of the micronized cellulose layer (coating layer) 2 can be measured using, for example, a cryo-TEM.

The type of polymerizable monomer that can be used in step c2 is the same as the type of polymerizable monomer that can be used in step a2 according to the first embodiment described above. Accordingly, the explanation thereof is omitted herein.

The following can be used as the formaldehyde reactant.

The formaldehyde reactant has reactivity with formaldehyde, and does not have at least one of an amino group and an amino group salt-forming group. The phrase "have reactivity with formaldehyde" as used herein means the ability to react with formaldehyde to convert it into another compound. That is, the above formaldehyde reactant contains a group that has reactivity with formaldehyde. Due to the composite particles 4 containing micronized cellulose 1 and formaldehyde reactant-containing core particles 3 according to the present embodiment, the formaldehyde is removed by conversion to another compound by the reaction with the formaldehyde reactant.

The formaldehyde reactant is preferably an organic compound. Examples of such formaldehyde reactants include compounds having one or two or more members selected from the group consisting of a group represented by the formula "—NH—" (hereinafter also abbreviated as ""—NH—" group") and a group in which the group represented by the formula "—NH—" forms a salt (hereinafter also abbreviated as ""—NH—" salt-forming group"). It is presumed that in the formaldehyde reactant, the "—NH—" group has reactivity with formaldehyde and that the "—NH—" salt-forming group itself, or an "—NH—" group converted from the "—NH—" salt-forming group, shows reactivity with formaldehyde.

Specifically, preferable examples of the formaldehyde reactant include those having one or two or more members selected from the group consisting of a group represented by the formula "—C(=O)—NH—" (an amide bond, hereinafter also abbreviated as ""—C(=O)—NH—" group"), a group represented by the formula "—NH—C(=O)—NH—" (hereinafter also abbreviated as ""—NH—C(=O)—NH—" group"), a group in which a group represented by the formula "—C(=O)—NH—" forms a salt (hereinafter also abbreviated as ""—C(=O)—NH—" salt-forming group"), a group in which a group represented by the formula "—NH—C(=O)—NH—" forms a salt (hereinafter also abbreviated as ""—NH—C(=O)—NH—" salt-forming group"), a group represented by the formula "=N—NH—" (hereinafter also abbreviated as ""=N—NH—" group"), a group represented by the formula "—HN—N(—)—NH—" (hereinafter also abbreviated as ""—HN—N(—)—NH—" group"), a group in which a group represented by the formula "=N—NH—" forms a salt (hereinafter also abbreviated as ""=N—NH—" salt-forming group"), and a group in which a group represented by the formula "—HN—N(—)—NH—" forms a salt (hereinafter also abbreviated as ""—HN—N(—)—NH—" salt-forming group"). Here, for example, the "—HN—N(—)—NH—" group means that nitrogen atoms of two "—NH—" groups and one another group are bonded to one nitrogen atom through a single bond.

In the "—NH—C(=O)—NH—" salt-forming group and the "—HN—N(—)—NH—" salt-forming group, the number of "—NH—" salt-forming groups may be one or two or more.

The formaldehyde reactant having a ring structure is preferably, for example, one having a cyclic ring skeleton formed by one or two or more members selected from the group consisting of an "—NH—" group and an "—NH—" salt-forming group; and more preferably one having a cyclic ring skeleton formed by one or two or more members selected from the group consisting of a "—C(=O)—NH—" group, a "—NH—C(=O)—NH—" group, a "—C(=O)—NH—" salt-forming group, an "—NH—C(=O)—NH—" salt-forming group, an "=N—NH—" group, an "—HN—N(—)—NH—" group, an "=N—NH—" salt-forming group, and an "—HN—N(—)—NH—" salt-forming group.

When the formaldehyde reactant has a ring structure, the number of ring members of the ring skeleton, that is, the number of atoms that form the ring skeleton, is preferably 5 to 7, and more preferably 5 or 6 in the case of a monocyclic ring, and is preferably 8 to 10 in the case of a polycyclic ring.

Particularly preferable examples of the formaldehyde reactant include hydantoin and salts thereof, 2-imidazolidinone and salts thereof, 5-pyrazolone and salts thereof, 3-pyrazolone and salts thereof, 1,2,4-triazol-3-one and salts thereof, phthalimide and salts thereof, glycoluril and salts thereof, pyrazole and salts thereof, 1,2,3-triazole and salts thereof, 1,2,4-triazole and salts thereof, 1,2,3-benzotriazole and salts thereof, and the like. The above-described hydantoin, 2-imidazolidinone, 5-pyrazolone, 3-pyrazolone, 1,2,4-triazol-3-one, phthalimide, glycoluril, pyrazole, 1,2,3-triazole, 1,2,4-triazole, and 1,2,3-benzotriazole each may be substituted.

The structures of hydantoin, 2-imidazolidinone, 5-pyrazolone, 3-pyrazolone, 1,2,4-triazol-3-one, phthalimide, glycoluril, pyrazole, 1,2,3-triazole, 1,2,4-triazole, and 1,2,3-benzotriazole are shown below.

Hydantoin, 2-imidazolidinone, 5-pyrazolone, 3-pyrazolone, 1,2,4-triazol-3-one, pyrazole, 1,2,3-triazole, and 1,2,4-triazole are all 5-membered ring compounds. Phthalimide and 1,2,3-benzotriazole are both 9-membered ring compounds. Glycoluril is an 8-membered ring compound.

The compounds shown herein are merely examples of formaldehyde reactants.

The weight ratio of the micronized cellulose fiber dispersion and the polymerizable monomer mixed with a formaldehyde reactant that can be used in step c2 is not particularly limited. For example, the amount of polymerizable monomer is preferably 1 part by mass or more and 50 parts by mass or less relative to 100 parts by mass of the micronized cellulose fibers. It is not preferable that the amount of polymerizable monomer is less than 1 part by mass, because the yield of the composite particles 4 tends to decrease. It is also not preferable that the amount of polymerizable monomer is more than 50 parts by mass, because it tends to be difficult to uniformly coat the polymerizable monomer droplets 5A with the micronized cellulose 1.

Moreover, in step c2 according to the present embodiment, the polymerizable monomer may previously contain a polymerization initiator, as in step c2 according to the first embodiment described above. The polymerization initiator etc. that can be added in step c2 according to the present embodiment are the same as the polymerization initiator etc. explained in step a2 according to the first embodiment. Accordingly, the explanation thereof is omitted herein.

(Step c3)

Step c3 is a step of polymerizing the polymerizable monomer droplets 5A in a state in which at least a part of the surface of the polymerizable monomer droplets 5A is coated with the micronized cellulose 1, to form core particles 3, thereby obtaining composite particles 4 in which at least a part of the surface of the core particles 3 is coated with the micronized cellulose 1, and the core particles 3 and the micronized cellulose 1 are inseparable from each other.

The method for polymerizing the polymerizable monomer is not particularly limited, and can be suitably selected depending on the type of polymerizable monomer used and the type of polymerization initiator used. For example, a suspension polymerization method can be used.

The specific suspension polymerization method is also not particularly limited, and a known method can be used. For example, it can be performed by heating, while stirring, the O/W emulsion produced in step c2, in which the polymerizable monomer droplets 5A containing a polymerization initiator are coated with the micronized cellulose 1 and stabilized. The stirring method is not particularly limited, and a known method can be used. Specifically, a disperser or a stirrer can be used. Alternatively, only heat treatment may be performed without stirring. Although the temperature conditions during heating can be suitably set depending on the type of polymerizable monomer and the type of polymerization initiator, the temperature of the suspension is preferably 20 degrees or more and 150 degrees or less. It is not preferable that the heating temperature is lower than 20 degrees, because the polymerization reaction rate tends to decrease. It is also not preferable that the heating temperature exceeds 150 degrees, because the micronized cellulose 1 may be modified. The time for the polymerization reaction can be suitably set depending on the type of polymerizable monomer and the type of polymerization initiator, but is generally about 1 to 24 hours. Further, the polymerization reaction may be carried out by treatment with ultraviolet irradiation, which is a kind of electromagnetic waves. In addition to electromagnetic waves, particle beams, such as electron beams, may also be used.

Through the steps described above, it is possible to produce spherical composite particles 4 in which core particles 3 are coated with micronized cellulose 1.

The method for collecting and purifying the composite particles 4 produced by the above method is the same as the collection and purification method explained in step a4 according to the first embodiment described above. Accordingly, the explanation thereof is omitted herein.

(Effects of Second Embodiment)

The composite particles 4 according to the present embodiment are novel composite particles that have improved or even excellent dispersion stability derived from micronized cellulose 1 on the surface of the composite particles 4, that have high biocompatibility, and that do not aggregate in a solvent.

Moreover, the dry solid containing the composite particles 4 according to the present embodiment is obtained as a fine powder, and there is no aggregation of particles. Therefore, the composite particles 4 obtained as a dry powder can be easily redispersed in a solvent, and even after redispersion, they show dispersion stability derived from the coating layer 2 of the micronized cellulose 1 bonded to the surface of the composite particles 4.

Furthermore, the method for producing composite particles 4 according to the present embodiment makes it possible to provide a novel method for producing composite particles 4, the method having a low environment load and capable of providing the composite particles in a simple manner.

In addition, the dry solid containing a composite of micronized cellulose 1 according to the present embodiment makes it possible to provide a dry solid in a form that can be redispersed in a solvent.

Moreover, the composite particles 4 according to the present embodiment make it possible to almost completely remove the solvent; thus, the following effects can be expected: reduction of transportation costs, reduction of risk of decay, improvement of addition efficiency as additives, and improvement of kneading efficiency for hydrophobic resins.

Furthermore, in the composite particles 4 according to the present embodiment, the particles of the formaldehyde reactant-containing polymer as the core particles 3 are coated with the cellulose nanofibers as the micronized cellulose 1. Therefore, the formaldehyde in the atmosphere gradually comes into contact with the reactant through the cellulose nanofibers as the micronized cellulose 1; thus, it can be expected that the formaldehyde removal effect is obtained continuously for a longer period of time.

As one of the mechanisms of decomposing formaldehyde etc. by the composite particles 4 according to the present embodiment, the following mechanism is considered. In the composite particles 4, the surface of the core particles 3 is coated with the micronized cellulose 1 inseparable from the core particles 3, whereby formaldehyde etc., in the atmosphere can migrate to the surface or the inside of the core particles 3 through the micronized cellulose 1. It is presumed that since the thus-migrating formaldehyde etc. in the atmosphere reacts with the formaldehyde reactant (functional component) encapsulated in the core particles 3, the formaldehyde is detoxified.

The second embodiment of the present invention was explained in detail above with reference to the drawings. However, specific configurations are not limited to this embodiment, and design changes and the like within a range not deviating from the spirit of the present invention are also included. Further, the components described in the above second embodiment and modifications thereof can be combined with each other as appropriate.

Third Embodiment

Next, a third embodiment of the present invention will be described. In the following description, the components common to those already explained are given the same reference signs, and duplicate descriptions are omitted.
<Wallpaper>

The wallpaper 9 according to the present embodiment comprises the composite particles 4 according to the second embodiment of the present invention.

Figure 8:
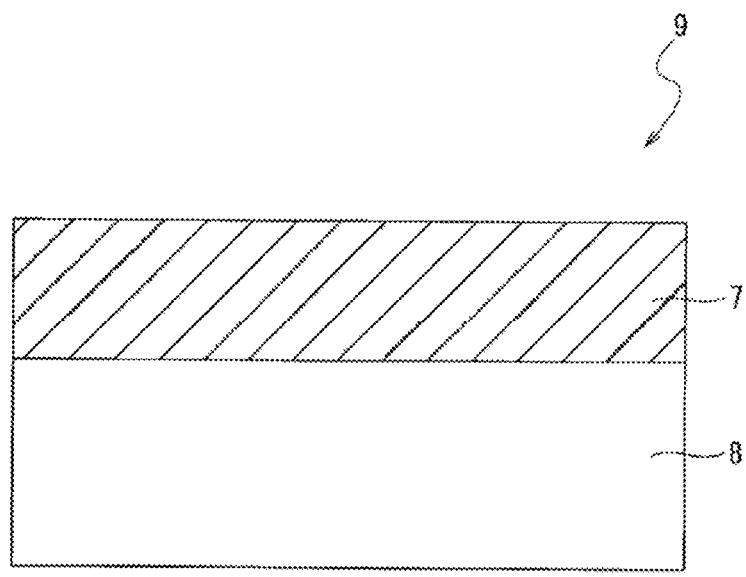
FIG. 8 is an enlarged view of an end face obtained by cutting the main part of wallpaper according to the second embodiment of the present invention.

The configuration of the wallpaper 9 is not particularly limited, as long as it is a sheet-like structure containing the composite particles 4; however, it is preferable that the composite particles 4 are exposed to the outermost surface, or that the surface of the composite particles 4 is coated with a moisture-permeable material. An example of the configuration of the wallpaper 9 is shown in FIG. 8, which shows wallpaper 9 provided with a functional layer 7 containing composite particles 4 on the upper side of a substrate 8.

The wallpaper 9 may be produced by applying a dispersion containing the composite particles 4 to the substrate 8 etc., or by molding a composition for wallpaper containing the composite particles 4. When a dispersion containing the composite particles 4 is applied to produce the wallpaper 9, the functional layer 7 is obtained by applying the dispersion containing the composite particles 4 to the substrate 8, and removing the solvent in the dispersion by heating or the like.

The dispersion containing the composite particles 4 may contain, if necessary, materials other than the composite particles 4 within a range that does not impair the effects of the present invention. Such materials are not particularly limited, and can be suitably selected from known additives depending on the application etc. of the wallpaper 9. Specific examples thereof include inorganic binders, such as condensates of alkoxysilanes; organic binders, such as acrylic resins and vinyl chloride resins; humidity conditioners, inorganic layered compounds, inorganic acicular minerals, antifoaming agents, inorganic particles, organic particles, lubricants, antioxidants, antistatic agents, ultraviolet absorbers, stabilizers, magnetic powders, orientation promoters, plasticizers, crosslinking agents, magnetic substances, drugs, pesticides, perfumes, adhesives, enzymes, pigments, dyes, deodorants, metals, metal oxides, inorganic oxides, and the like.

Examples of the material of the substrate 8 include non-woven fabric, mesh, paper, pulp, polyethylene terephthalate (PET), polypropylene (PP), polyethylene terephthalate glycol-modified (PETG), polyvinyl chloride (PVC), glass, silicon, and the like. Further, the substrate 8 may be surface-modified with, for example, but not limited to, indium-tin oxide (ITO) or silicon oxide (SiOx). The substrate 8 may be transparent, opaque, or reflective. Moreover, the substrate 8 may have any color, such as black or white, according to the intended use of the wallpaper 9. Further, the substrate 8 may or may not have gloss. The substrate 8 may be omitted.

Usable examples of the means for applying the dispersion containing the composite particles 4 to the substrate 8 etc. include brush coating, trowel coating, bar coater, knife coater, doctor blade, screen printing, spray coating, spin coating, applicator, roll coating, flow coating, centrifugal coating, ultrasonic coating, (micro)gravure coating, dip coating, flexographic printing, potting, sweep treatment, and other means. The dispersion may be applied to another substrate, such as a transfer substrate, and then transferred. Moreover, coating of the dispersion containing the composite particles 4 may be performed not only once, but also several times. When a solvent is contained in the dispersion containing the composite particles 4, it is necessary to remove the solvent, for example, by heating and drying at a temperature at which the solvent can be removed.

In FIG. 8, the wallpaper 9 is constituted from the functional layer 7 and the substrate 8; however, another functional layer different from the functional layer 7 can be provided, if necessary, within a range that does not impair the hygroscopic properties of the wallpaper 9. Examples of the roles of the functional layers other than the functional layer 7 include prevention of the functional layer 7 from being damaged, and prevention of the functional layer 7 from being contaminated.
(Effects of Third Embodiment)

The wallpaper 9 according to the present embodiment allows the reaction with chemical substances that are highly compatible with the micronized cellulose 1, as in the second embodiment. In particular, the wallpaper 9 according to the present embodiment allows the composite particles 4 to react with formaldehyde to thereby remove the formaldehyde from the atmosphere.

The third embodiment of the present invention has been explained in detail above with reference to the drawings. However, specific configurations are not limited to this embodiment, and design changes and the like within a range not deviating from the spirit of the present invention are also included. Further, the components described in the above first to third embodiments can be combined with each other as appropriate.

Second Examples

Hereinafter, the present invention will be described in detail based on second examples. However, the technical scope of the present invention is not limited to these examples. In the following examples, % indicates % by mass (w/w %) unless otherwise noted.

Example 2-1

(Step c1: Step of Obtaining Micronized Cellulose Dispersion)
(TEMPO Oxidation of Wood Cellulose)

70 g of softwood kraft pulp was suspended in 3500 g of distilled water, and a solution obtained by dissolving 0.7 g of TEMPO and 7 g of sodium bromide in 350 g of distilled water was added, followed by cooling to 20° C. 450 g of sodium hypochlorite aqueous solution with 2 mol/L and a density of 1.15 g/mL was added dropwise, whereby the oxidation reaction was started. The temperature in the system was kept constant at 20° C. The pH was prevented from lowering by being kept at pH 10 by adding a 0.5 N sodium hydroxide aqueous solution. When the total amount of sodium hydroxide added reached 3.50 mmol/g based on the weight of cellulose, approximately 100 mL of ethanol was added to stop the reaction. Thereafter, filtering and washing were repeated with distilled water by means of a glass filter, whereby oxidized pulp (oxidized cellulose) was obtained.
(Measurement of the Amount of Carboxyl Groups in Oxidized Pulp)

The oxidized pulp and reoxidized pulp obtained by TEMPO oxidation were weighed at a solid content weight of 0.1 g and dispersed in water at a concentration of 1%, and hydrochloric acid was added to adjust the pH to 2.5. Thereafter, the amount of carboxyl groups (mmol/g) was determined by conductometric titration using a 0.5 M sodium hydroxide aqueous solution. The result was 1.6 mmol/g.
(Fibrillation Treatment of Oxidized Pulp)

1 g of the oxidized pulp obtained by TEMPO oxidization was dispersed in 99 g of distilled water, and micronized by a juicer mixer for 30 minutes to obtain a CSNF water dispersion with a CSNF concentration of 1%. The CSNF dispersion was put in a quartz cell with an optical path length of 1 cm, and the spectral transmission spectrum was measured using a spectrophotometer ("UV-3600," produced by Shimadzu Corporation). FIG. 4 shows the results. As is clear from FIG. 4, the CSNF water dispersion showed a high transparency. The number average minor axis diameter of CSNF contained in the CSNF water dispersion was 3 nm, and the number average major axis diameter of the CSNF was 1110 nm. Further, FIG. 5 shows the results of static viscoelasticity measurement using a rheometer. As is clear from FIG. 5, the CSNF dispersion was thixotropic.
(Step c2: Step of Producing O/W Emulsion)

Next, 1 g of 2,2-azobis-2,4-dimethylvaleronitrile (hereinafter also referred to as ADVN) as a polymerization initiator was dissolved in 10 g of divinylbenzene (hereinafter also referred to as DVB) as a polymerizable monomer. Further, as a formaldehyde reactant, 5,5-dimethylhydantoin (1 g, produced by Tokyo Kasei Kogyo Co., Ltd.) was added and dissolved. When the total amount of the DVB/ADVN/5,5-dimethylhydantoin mixture was added to 40 g of CSNF dispersion with a CSNF concentration of 1%, the DVB/ADVN/5,5-dimethylhydantoin mixture and the CSNF dispersion were separated into two phases each in a highly transparent state.

Next, the shaft of an ultrasonic homogenizer was inserted via the liquid surface of the upper phase in the mixture in the two-phase separated state, and ultrasonic homogenizer treatment was carried out for 3 minutes at a frequency of 24 kHz and an output of 400 W. The appearance of the mixture after ultrasonic homogenizer treatment resembled a cloudy emulsion. When a drop of the mixture was added to a glass slide, sealed with cover glass, and observed with a light microscope, it was confirmed that an enormous number of emulsion droplets in size of about 1 to several μm were formed, and that they were dispersed and stabilized as an O/W emulsion.
(Step c3: Step of Obtaining Composite Particles 4 Coated with CNF by Polymerization Reaction)

The O/W emulsion dispersion was placed in a hot-water bath at 70° C., and treated by stirring with a stirrer for 8 hours to carry out the polymerization reaction. The dispersion was cooled to room temperature after the 8-hour treatment. The appearance of the dispersion did not change before and after the polymerization reaction. When the obtained dispersion was treated at a centrifugal force of 75,000 g (g: gravitational acceleration) for 5 minutes, a precipitate was obtained. The supernatant was removed by decantation, and the precipitate was collected. Further, the precipitate was repeatedly washed with purified water and methanol using a PTFE membrane filter with a pore size of 0.1 μm. The thus-obtained purified and collected product was redispersed at a concentration of 1%, and the particle size was evaluated using a particle size distribution meter (Nanotrac UPA-EX150, produced by Nikkiso Co., Ltd.). As a result, the average particle size was found to be 2.1 μm. Next, the purified and collected product was air-dried, and further vacuum-dried at room temperature (25° C.) for 24 hours. As a result, a fine dry powder (composite particles 4) was obtained.

(Shape Observation with Scanning Electron Microscope)

FIGS. 6 and 7 show the results of observing the obtained dry powder with a scanning electron microscope. As is clear from FIG. 6, it was confirmed that the polymerization reaction performed using O/W emulsion droplets as a template resulted in the formation of an enormous number of spherical composite particles 4 derived from the shape of the emulsion droplets. Further, as shown in FIGS. 7 (a) and (b), it was confirmed that their surface was uniformly coated with several-nanometer-wide micronized cellulose 1. Moreover, the surface of the composite particles 4 was equally and uniformly coated with the micronized cellulose 1, even after washing was repeated by filtration washing. Therefore, it was indicated that in the composite particles 4 of the present embodiment, the monomer (core particles 3) inside the composite particles 4 and the micronized cellulose 1 were may be bonded, and that the core particles 3 and the micronized cellulose 1 were inseparable from each other.
(Evaluation of Redispersibility)

When the dry powder of the composite particles 4 was added to purified water at a concentration of 1% and redispersed by a stirrer, the dry powder was easily redispersed, and no aggregation was observed. Moreover, when the particle size was evaluated using a particle size distribution meter, the average particle size was 2.1 μm as with that before drying, and the data from the particle size distribution meter did not show any signal indicating aggregation.

The above results indicated that although the surface of the composite particles 4 was coated with the micronized cellulose 1, they were obtained as a powder by drying without forming a film, and had improved or even excellent redispersibility.
(Evaluation of Long-Term Continuity of Formaldehyde Removal)

As a method for confirming the formaldehyde removal effect of the composite particles 4, a plurality of chambers filled with formaldehyde were prepared, wallpaper 9 coated with a dispersion containing the composite particles 4 was put in a chamber A, and the formaldehyde concentration in the chamber A was measured after the lapse of a predetermined period of time. The same wallpaper 9 used on day 1 was put in a new chamber B, and the formaldehyde concentration in the chamber B was measured after the lapse of a predetermined period of time to confirm the effect. This operation was repeated for several days, and the number of days in which the formaldehyde removal effect continued was counted.

Example 2-2

Composite particles 4 according to Example 2-2 were produced in the same manner as in Example 2-1, except that diethylene glycol diacrylate (trade name: FA-222A, Hitachi Chemical Co., Ltd.; hereinafter also referred to as FA-222A) was used in place of DVB in Example 2-1, and various evaluations were carried out in the same manner.

Example 2-3

Composite particles 4 according to Example 2-3 were produced in the same manner as in Example 2-1, except that hexanediol diacrylate (trade name: A-HD-N, Shin Nakamura Chemical Co., Ltd.; hereinafter also referred to as A-HD-N) was used in place of DVB in Example 2-1.

Example 2-4

Composite particles 4 according to Example 2-4 were produced under the same conditions as in Example 2-1, except that 2-imidazolidinone (1 g, produced by Tokyo Kasei Kogyo Co., Ltd.) was used in place of 5,5-dimethylhydantoin (1 g, produced by Tokyo Kasei Kogyo Co., Ltd.) in Example 1, and various evaluations were carried out in the same manner.

Example 2-5

Composite particles 4 according to Example 2-5 were produced under the same conditions as in Example 2-1, except that 3-methyl-5-pyrazolone (1 g, produced by Tokyo Kasei Kogyo Co., Ltd.) was used in place of 5,5-dimethylhydantoin (1 g, produced by Tokyo Kasei Kogyo Co., Ltd.) in Example 2-1, and various evaluations were carried out in the same manner.

Comparative Example 2-1

An attempt was made to produce composite particles according to Comparative Example 2-1 under the same conditions as in Example 2-1, except that adipic acid dihydrazide (1 g, produced by Tokyo Kasei Kogyo Co., Ltd.) was used in place of 5,5-dimethylhydantoin (1 g, produced by Tokyo Kasei Kogyo Co., Ltd.) in Example 2-1.

Comparative Example 2-2

An attempt was made to produce composite particles according to Comparative Example 2-2 under the same conditions as in Example 2-1, except that sebacic acid dihydrazide (1 g, produced by Tokyo Kasei Kogyo Co., Ltd.) was used in place of 5,5-dimethylhydantoin (1 g, produced by Tokyo Kasei Kogyo Co., Ltd.) in Example 2-1.

Comparative Example 2-3

An attempt was made to produce composite particles according to Comparative Example 2-4 under the same conditions as in Example 2-1, except that aminoethyl ethanol (1 g, produced by Tokyo Kasei Kogyo Co., Ltd.) was used in place of 5,5-dimethylhydantoin (1 g, produced by Tokyo Kasei Kogyo Co., Ltd.) in Example 2-1.

The following Table 5 collectively shows the evaluation results using Examples 2-1 to 2-5 and Comparative Examples 2-1 to 2-3.

In Comparative Examples 2-1 to 2-3, the use of formaldehyde reactants having an amino group or an amino group salt-forming group caused a reaction with the carboxylic acid of CNF, and the coating of the core particles 3 with CNF was inhibited. As a result, CNF coating failed.

In Table 5, whether step c2 could be performed was determined as follows.
++: An O/W emulsion could be formed.
−: An O/W emulsion could not be formed.
Further, whether step c3 could be performed was determined as follows.
++: Spherical particles using the emulsion of step c3 as a template were obtained.
−: Such particles were not obtained.
The redispersibility was determined as follows.
++: Composite particles could be redispersed in solvent.
−: Composite particles could not be redispersed in solvent.
The long-term continuity of the formaldehyde removal effect was determined as follows.
++: The effect was continued for 10 days or more.
+: The effect was continued for 2 days or less.
The oblique lines in the cells of the comparative examples in Table 5 indicate that each step could not be conducted during implementation of the step, and that the subsequent step was not carried out.

As is clear from the evaluation results of Examples 2-1 to 2-5 in Table 5, it was confirmed that formaldehyde-containing polymer particles coated with cellulose nanofibers could be produced by selecting the type of monomer and a formaldehyde reactant within a specific range. Moreover, as is clear from the evaluation results of Examples 2-1 to 2-5 in Table 5, it was confirmed that the formaldehyde removal effect could be continued for a long period of time by selecting the type of monomer and a formaldehyde reactant within a specific range. Even if the formaldehyde removal effect is continued for two days or less, there is no problem in use.

On the other hand, in Comparative Examples 2-1 to 2-3, an O/W emulsion could be formed in step c2; however, the emulsion was destabilized when the polymerization reaction was carried out in the subsequent step c3, and composite particles using the O/W emulsion as a template could not be obtained. Although the reason for this is not clear, it is considered that the carboxyl groups on the cellulose nanofiber surface reacted with the formaldehyde reactant, whereby the emulsion was destabilized during the polymerization reaction.

INDUSTRIAL APPLICABILITY

The sustained-release composite particles 4 of the present invention protect functional components from ultraviolet rays, heat, oxygen, etc., due to the characteristics of the micronized cellulose 1 (cellulose nanofibers), such as gas

TABLE 5

| | Monomer | Formaldehyde reactant | Possibility of step c2 | Possibility of step c3 | Long-term continuity of formaldehyde removal | Redispersibility |
|---|---|---|---|---|---|---|
| Example 2-1 | DVB | 5,5-Dimethylhydantoin | ++ | ++ | ++ | ++ |
| Example 2-2 | FA-222A | 5,5-Dimethylhydantoin | ++ | ++ | ++ | ++ |
| Example 2-3 | A-HD-N | 5,5-Dimethylhydantoin | ++ | ++ | ++ | ++ |
| Example 2-4 | DVB | 2-Imidazolidinone | ++ | ++ | ++ | ++ |
| Example 2-5 | DVB | 3-Methyl-5-pyrazolone | ++ | ++ | ++ | ++ |
| Comparative Example 2-1 | DVB | Adipic acid dihydrazide | ++ | − | + | |
| Comparative Example 2-2 | DVB | Sebacic acid dihydrazide | ++ | − | + | |
| Comparative Example 2-3 | DVB | Aminoethyl ethanol | ++ | − | + | | barrier properties, hydrophilicity, heat resistance, and high strength; have improved or even excellent sustained-release properties and exhibit long-term effects; can reduce the number of times functional components, such as pesticides and fertilizers, are used; and are preferable from the viewpoints of economic efficiency and environmental impact.

The sustained-release composite particles 4 can encapsulate most of the raw materials of functional components and are thus economical, and there is little pollution due to disposal thereof. Further, the micronized cellulose 1 is fibrous cellulose composed of cellulose, which is a biodegradable polymer. When a biodegradable polymer is used as the polymer contained in the core particles 3, it is decomposed when used as a pesticide, fertilizer, or the like, and is safe, thereby suppressing environmental pollution.

[Reference Signs List] 1 . . . Micronized cellulose (cellulose nanofiber); 2 . . . Coating layer (micronized cellulose layer); 3 . . . Core particle (polymer+functional component); 4 . . . Composite particle; 5 . . . Droplet; 5A . . . Droplet (polymerizable monomer droplet) (monomer+functional component); 5B . . . Droplet (polymer droplet) (polymer+functional component+organic solvent); 6 . . . Dispersion (water); 7 . . . Functional layer; 8 . . . Substrate; 9 . . . Wallpaper.

What is claimed is:

1. Sustained-release composite particles, comprising:
   active core particles comprising a mixture of at least one polymer and at least one functional component, and,
   an inert coating on the surface of the inert core particles,
   the inert coating consists essentially of micronized cellulose,
   the micronized cellulose is uniformly coated on the surface of the inert core particles,
   the at least one functional component is selected from the group consisting of an antifungal agent, a perfume, a fertilizer, a pesticide, a plant activator, a plant life extender, a pest and animal repellent, a soil penetrant, a nutrient component, a plant hormone, an antibacterial substance and combinations thereof, and
   the active core particles and the micronized cellulose of the inert coating being inseparable from each other.

2. The sustained-release composite particles of claim 1, wherein
   the micronized cellulose comprises a crystallized surface, and,
   the crystallized surface of the micronized cellulose comprises an anionic functional group.

3. The sustained-release composite particles of claim 1, wherein the functional component is a formaldehyde reactant.

4. The sustained-release composite particles of claim 3, wherein the formaldehyde reactant has reactivity with formaldehyde and does not have at least one of an amino group and a group in which an amino group forms a salt.

5. A wallpaper product comprising the sustained-release composite particles of claim 1.

6. The sustained-release composite particles of claim 1, wherein the inert core particles are prepared by polymerizing at least one polymerizable monomer in a polymerizable monomer mixture comprising the at least one polymerizable monomer and the at least one functional component.

7. The sustained-release composite particles of claim 6, wherein the at least one polymerizable monomer comprises a monomer having a vinyl group.

8. The sustained-release composite particles of claim 6, wherein the at least one polymerizable monomer comprises a monomer having a (meth)acrylic group.

9. The sustained-release composite particles of claim 6, wherein the at least one polymerizable monomer comprises a polyfunctional monomer having two or more polymerizable functional groups.

10. The sustained-release composite particles of claim 9, wherein at least one of the two or more polymerizable functional groups in the polyfunctional monomer is a vinyl group.

11. The sustained-release composite particles of claim 10, wherein the polyfunctional monomer is divinylbenzene.

12. The sustained-release composite particles of claim 9, wherein at least one of the two or more polymerizable functional groups in the polyfunctional monomer is a (meth)acrylic group.

13. The sustained-release composite particles of claim 1, wherein the polymer is a biodegradable polymer.

14. A dry powder comprising the sustained-release composite particles of claim 1.

15. The dry powder of claim 14, wherein the dry powder has a solid content of 80% or more.

16. A method for producing sustained-release composite particles according to claim 1, comprising the steps of:
   step a1 of defibrating a cellulose raw material in a solvent to obtain a dispersion of micronized cellulose;
   step a2 of preparing a monomer mixture containing at least one type of polymerizable monomer and at least one type of functional component;
   step a3 of coating, with the micronized cellulose, at least a part of the surface of polymerizable monomer droplets composed of the monomer mixture containing the polymerizable monomer and the functional component in the dispersion of the micronized cellulose to stabilize the polymerizable monomer droplets as an emulsion; and,
   step a4 of polymerizing the polymerizable monomer droplets in a state in which at least a part of the surface of the polymerizable monomer droplets is coated with the micronized cellulose to form core particles containing a polymer and the functional component, thereby coating at least a part of the surface of the core particles with the micronized cellulose, and making the core particles and the micronized cellulose inseparable from each other.

17. The method for producing sustained-release composite particles of claim 16, wherein the functional component is a formaldehyde reactant.

18. A method for producing sustained-release composite particles according to claim 1, comprising the steps of:
   step b1 of fibrillating a cellulose raw material in a solvent to obtain a dispersion of micronized cellulose;
   step b2 of preparing a polymer solution by adding and dissolving at least one type of polymer and at least one type of functional component in an organic solvent capable of dissolving the polymer;
   step b3 of coating, with the micronized cellulose, at least a part of the surface of polymer droplets composed of the polymer solution containing the polymer, the functional component, and the organic solvent in the dispersion of the micronized cellulose to stabilize the polymer droplets as an emulsion; and,
   step b4 of removing the organic solvent contained in the polymer droplets to solidify the polymer in a state in which at least a part of the surface of the polymer droplets is coated with the micronized cellulose to form core particles containing the polymer and the functional component, thereby coating at least a part of the surface of the core particles with the micronized cellulose, and making the core particles and the micronized cellulose inseparable from each other.

\* \* \* \* \*